US009265252B2

(12) United States Patent
Deall et al.

(10) Patent No.: US 9,265,252 B2
(45) Date of Patent: Feb. 23, 2016

(54) ACTIVE COMPOUND COMBINATIONS COMPRISING SPECIFIC TETRAMIC ACID DERIVATIVES

(75) Inventors: Michael Deall, Burscheid (DE); Reiner Fischer, Monheim (DE); Erwin Hacker, Langenenslingen (DE); Heike Hungenberg, Langenfeld (DE); John Bell, Chapel Hill, NC (US); Robert Steffens, Cary, NC (US)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/233,661

(22) PCT Filed: Aug. 7, 2012

(86) PCT No.: PCT/EP2012/065469
§ 371 (c)(1),
(2), (4) Date: Feb. 18, 2014

(87) PCT Pub. No.: WO2013/020985
PCT Pub. Date: Feb. 14, 2013

(65) Prior Publication Data
US 2014/0208463 A1    Jul. 24, 2014

Related U.S. Application Data

(60) Provisional application No. 61/521,827, filed on Aug. 10, 2011.

(51) Int. Cl.
| *A01N 47/06* | (2006.01) |
| *A01N 57/20* | (2006.01) |
| *A01N 25/32* | (2006.01) |
| *A01N 43/38* | (2006.01) |

(52) U.S. Cl.
CPC ............... *A01N 43/38* (2013.01); *A01N 25/32* (2013.01); *A01N 47/06* (2013.01); *A01N 57/20* (2013.01)

(58) Field of Classification Search
CPC ........ A01N 47/06; A01N 43/38; A01N 25/32
See application file for complete search history.

(56) References Cited

U.S. PATENT DOCUMENTS

| 4,213,773 A | 7/1980 | Wolf |
| 4,384,880 A | 5/1983 | Large |
| 4,761,373 A | 8/1988 | Anderson et al. |
| 5,013,659 A | 5/1991 | Bedbrook et al. |
| 5,084,082 A | 1/1992 | Sebastian |
| 5,141,870 A | 8/1992 | Bedbrook et al. |
| 5,163,995 A | 11/1992 | Van Heertum et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,378,824 A | 1/1995 | Bedbrook et al. |
| 5,434,283 A | 7/1995 | Wong et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,789,566 A | 8/1998 | Bonhomme et al. |
| 5,792,923 A | 8/1998 | Rober et al. |
| 5,824,790 A | 10/1998 | Keeling et al. |
| 5,840,946 A | 11/1998 | Wong et al. |
| 5,846,907 A | 12/1998 | Von Deyn et al. |
| 5,866,782 A | 2/1999 | Iwabuchi et al. |
| 5,908,810 A | 6/1999 | Donn |
| 5,908,975 A | 6/1999 | Caimi et al. |
| 5,928,937 A | 7/1999 | Kakefuda et al. |
| 5,965,755 A | 10/1999 | Sernyk et al. |

(Continued)

FOREIGN PATENT DOCUMENTS

| AU | 652964 | 4/1992 |
| AU | 738279 B2 | 9/2001 |

(Continued)

OTHER PUBLICATIONS

Bruck, E. et al., "Movento, an innovative ambimobile insecticide for sucking insect pest control in agriculture: Biological profile and field performance," Crop Protection, vol. 28, pp. 838-844 (2009).*
Joseph H. Pankey, et al., "Glyphosate-Insecticide Combination Effects on Weed and Insect Control in Cotton", Weeky Technology, (2004), vol. 18 (3): 689-703.
International Search Report received in PCT/EP2012/065469, mailed Nov. 11, 2012.
Schnepf, et al., Characterization of Cry34/Cry35 Binary Insecticidal Proteins from Diverse Bacillus thuringiensis Strain Collections, Applied and Environmental Microbiology, Apr. 2005, pp. 1765-1774.
Barry, et al., "Inhibitors of Amino Acid Biosynthesis: Strategies for Imparting Glyphosate Tolerance to Crop Plants", Current Topics in Plant Physiology, 1993, vol. 7, pp. 139-145.
Soltani, et al., "Co-application of Glyphosate Plus an Insecticide or Fungicide in Glyphosate-Resistant Soybean", Canadian Journal of Plant Science, 2012, 92, pp. 297-302.

(Continued)

*Primary Examiner* — John Pak
(74) *Attorney, Agent, or Firm* — Miles & Stockbridge P.C.

(57) ABSTRACT

The invention provides combinations of insecticides/acaricides and herbicides comprising an effective amount of components (A) and (B), where component (A) is one or more of the tetramic acid derivatives listed in the description, and (B) one or more herbicides from the group of the herbicides likewise listed in the description, where the combinations may optionally additionally comprise crop plant compatibility-increasing substances (safeners).
The invention also relates to the use of the combinations for controlling animal pests and unwanted vegetation and to the corresponding methods.

17 Claims, No Drawings

(56) References Cited

U.S. PATENT DOCUMENTS

| | | |
|---|---|---|
| 5,969,169 A | 10/1999 | Fan |
| 6,013,861 A | 1/2000 | Bird et al. |
| 6,040,497 A | 3/2000 | Spencer et al. |
| 6,063,947 A | 5/2000 | DeBonte et al. |
| 6,066,782 A | 5/2000 | Kossmann et al. |
| 6,114,374 A | 9/2000 | Lieb et al. |
| 6,130,367 A | 10/2000 | Kossmann et al. |
| 6,162,966 A | 12/2000 | Kossmann et al. |
| 6,169,190 B1 | 1/2001 | Lanuza et al. |
| 6,207,880 B1 | 3/2001 | Kossmann et al. |
| 6,211,436 B1 | 4/2001 | Kossmann et al. |
| 6,215,042 B1 | 4/2001 | Willmitzer et al. |
| 6,229,072 B1 | 5/2001 | Burns et al. |
| 6,245,968 B1 | 6/2001 | Boudec et al. |
| 6,255,342 B1 | 7/2001 | Lieb et al. |
| 6,255,561 B1 | 7/2001 | Kossman et al. |
| 6,255,563 B1 | 7/2001 | Emmermann et al. |
| 6,268,549 B1 | 7/2001 | Sailland et al. |
| 6,270,828 B1 | 8/2001 | DeBonte et al. |
| 6,284,479 B1 | 9/2001 | Nichols |
| 6,294,712 B1 | 9/2001 | Kleine et al. |
| 6,307,124 B1 | 10/2001 | Kossmann et al. |
| 6,323,392 B1 | 11/2001 | Charne |
| 6,359,151 B2 | 3/2002 | Lieb et al. |
| 6,376,429 B1 | 4/2002 | Van Almsick et al. |
| 6,504,036 B1 | 1/2003 | Lieb et al. |
| 6,566,585 B1 | 5/2003 | Quanz |
| 6,566,587 B1 | 5/2003 | Lebrun et al. |
| 6,590,141 B1 | 7/2003 | Frohberg |
| 6,596,873 B1 | 7/2003 | Lieb et al. |
| 6,596,928 B1 | 7/2003 | Landschutze |
| 6,699,694 B1 | 3/2004 | Buttcher et al. |
| 6,734,341 B2 | 5/2004 | Singletary et al. |
| 6,791,010 B1 | 9/2004 | Frohberg |
| 6,794,558 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 6,897,358 B2 | 5/2005 | Loerz et al. |
| 7,112,665 B1 | 9/2006 | Leemans et al. |
| 7,112,718 B2 | 9/2006 | Uwer et al. |
| 7,157,281 B2 | 1/2007 | Dizigan et al. |
| 7,304,209 B2 | 12/2007 | Zink et al. |
| 7,335,816 B2 | 2/2008 | Kraus et al. |
| 7,435,807 B1 | 10/2008 | Barbour et al. |
| 7,576,264 B2 | 8/2009 | Dogimont et al. |
| 7,638,547 B2 | 12/2009 | Himmler et al. |
| 7,834,168 B2 | 11/2010 | Trolinder et al. |
| 7,897,803 B2 | 3/2011 | Himmler et al. |
| 2002/0010204 A1 | 1/2002 | Lieb et al. |
| 2002/0031826 A1 | 3/2002 | Nichols |
| 2002/0065200 A1 | 5/2002 | Schmitt et al. |
| 2003/0126634 A1 | 7/2003 | Spencer et al. |
| 2004/0117870 A1 | 6/2004 | Weyens et al. |
| 2004/0148666 A1 | 7/2004 | Rangwala et al. |
| 2004/0177399 A1 | 9/2004 | Hammer et al. |
| 2004/0180373 A1 | 9/2004 | Levine |
| 2004/0197916 A1 | 10/2004 | Carozzi et al. |
| 2004/0210964 A1 | 10/2004 | Carozzi et al. |
| 2004/0216186 A1 | 10/2004 | Carozzi et al. |
| 2004/0250317 A1 | 12/2004 | Huber et al. |
| 2005/0257283 A1 | 11/2005 | Matringe et al. |
| 2006/0015966 A1 | 1/2006 | Landschutze |
| 2006/0021093 A1 | 1/2006 | Hammer et al. |
| 2006/0070139 A1 | 3/2006 | Bing et al. |
| 2006/0095986 A1 | 5/2006 | Cavato et al. |
| 2006/0115545 A1 | 6/2006 | Frohberg et al. |
| 2006/0130175 A1 | 6/2006 | Ellis et al. |
| 2006/0150269 A1 | 7/2006 | Hammer et al. |
| 2006/0150270 A1 | 7/2006 | Hammer et al. |
| 2006/0150278 A1 | 7/2006 | Frohberg et al. |
| 2006/0162007 A1 | 7/2006 | Guo et al. |
| 2006/0168690 A1 | 7/2006 | Shibatani et al. |
| 2006/0230473 A1 | 10/2006 | Johnson et al. |
| 2006/0242732 A1 | 10/2006 | Carozzi et al. |
| 2006/0248612 A1 | 11/2006 | Vancanneyt et al. |
| 2006/0253921 A1 | 11/2006 | Carozzi et al. |
| 2006/0253929 A1 | 11/2006 | Frohberg |
| 2006/0282915 A1 | 12/2006 | Malven et al. |
| 2007/0004907 A1 | 1/2007 | Hammer et al. |
| 2007/0011777 A1 | 1/2007 | Frohberg |
| 2007/0022496 A1 | 1/2007 | Moor et al. |
| 2007/0032539 A1 | 2/2007 | Himmler |
| 2007/0056056 A1 | 3/2007 | Behr et al. |
| 2007/0067868 A1 | 3/2007 | Negrotto et al. |
| 2007/0107078 A1 | 5/2007 | Hammer et al. |
| 2007/0136840 A1 | 6/2007 | Peters et al. |
| 2007/0163003 A1 | 7/2007 | Frohberg et al. |
| 2007/0169218 A1 | 7/2007 | Carr et al. |
| 2007/0289035 A1 | 12/2007 | Vande Berg et al. |
| 2007/0292854 A1 | 12/2007 | Behr et al. |
| 2008/0064032 A1 | 3/2008 | Townshend et al. |
| 2008/0167188 A1 | 7/2008 | Fischer et al. |
| 2008/0176801 A1 | 7/2008 | Carozzi et al. |
| 2008/0196127 A1 | 8/2008 | De Beuckeleer |
| 2008/0250533 A1 | 10/2008 | Frohberg |
| 2008/0251225 A1 | 10/2008 | Landschuetze et al. |
| 2008/0276336 A1 | 11/2008 | Frohberg et al. |
| 2008/0289060 A1 | 11/2008 | De Beuckeleer et al. |
| 2008/0312419 A1 | 12/2008 | Hammer et al. |
| 2009/0013431 A1 | 1/2009 | Van Thournout et al. |
| 2009/0028837 A1 | 1/2009 | De Block et al. |
| 2009/0044291 A1 | 2/2009 | Zhang et al. |
| 2009/0064371 A1 | 3/2009 | Metzlaff et al. |
| 2009/0064372 A1 | 3/2009 | Kok-Jacon et al. |
| 2009/0100543 A1 | 4/2009 | Carozzi et al. |
| 2009/0105469 A1 | 4/2009 | Soyka et al. |
| 2009/0106863 A1 | 4/2009 | Frohberg et al. |
| 2009/0119797 A1 | 5/2009 | Hammer et al. |
| 2009/0126044 A1 | 5/2009 | Carozzi et al. |
| 2009/0151016 A1 | 6/2009 | Frohberg et al. |
| 2009/0151018 A1 | 6/2009 | Hammer et al. |
| 2009/0151021 A1 | 6/2009 | Bots et al. |
| 2009/0181399 A1 | 7/2009 | Negrotto et al. |
| 2009/0193545 A1 | 7/2009 | Watson |
| 2009/0199311 A1 | 8/2009 | Frohberg et al. |
| 2009/0203075 A1 | 8/2009 | Hammer et al. |
| 2009/0209513 A1 | 8/2009 | Fischer et al. |
| 2009/0227771 A1 | 9/2009 | Peters et al. |
| 2009/0270605 A1 | 10/2009 | Soyka et al. |
| 2009/0300798 A1 | 12/2009 | Kok-Jacon et al. |
| 2009/0313717 A1 | 12/2009 | Hernandez et al. |
| 2009/0317535 A1 | 12/2009 | Frohberg et al. |
| 2009/0320154 A1 | 12/2009 | De Block et al. |
| 2010/0034953 A1 | 2/2010 | Frohberg |
| 2010/0050282 A1 | 2/2010 | Trolinder et al. |
| 2010/0056598 A1 | 3/2010 | Himmler et al. |
| 2010/0077501 A1 | 3/2010 | Trolinder et al. |
| 2010/0083404 A1 | 4/2010 | Ogawa et al. |
| 2010/0113273 A1 | 5/2010 | Takabe et al. |
| 2010/0130366 A1 | 5/2010 | Andersch et al. |
| 2010/0199764 A1 | 8/2010 | Hammer |
| 2010/0218281 A1 | 8/2010 | Trolinder et al. |
| 2010/0235951 A1 | 9/2010 | Van Rie et al. |
| 2010/0292461 A1 | 11/2010 | Hoehne et al. |
| 2010/0316786 A1 | 12/2010 | Frohberg |
| 2010/0317058 A1 | 12/2010 | Frohberg |
| 2011/0023189 A1 | 1/2011 | Takahashi et al. |
| 2011/0030106 A1 | 2/2011 | Laga et al. |
| 2011/0039700 A1 | 2/2011 | Fischer |
| 2011/0047646 A1 | 2/2011 | Manzanero |
| 2011/0053919 A1 | 3/2011 | Fischer et al. |
| 2011/0078818 A1 | 3/2011 | Kondo et al. |
| 2011/0093970 A1 | 4/2011 | Arioli et al. |
| 2011/0119790 A1 | 5/2011 | Fujino et al. |
| 2011/0126312 A1 | 5/2011 | Navarro Avino |
| 2011/0131672 A1 | 6/2011 | De Block et al. |
| 2011/0145944 A1 | 6/2011 | Laga et al. |
| 2011/0239330 A1 | 9/2011 | Kondo et al. |
| 2011/0252500 A1 | 10/2011 | Murigneux et al. |
| 2011/0268865 A1 | 11/2011 | Kebeish et al. |
| 2011/0269195 A1 | 11/2011 | Frohberg et al. |
| 2011/0294127 A1 | 12/2011 | De Beuckeleer |
| 2011/0294783 A1 | 12/2011 | Fischer et al. |

(56) References Cited

U.S. PATENT DOCUMENTS

| | | |
|---|---|---|
| 2012/0023603 A1 | 1/2012 | Laga et al. |
| 2012/0255051 A1 | 10/2012 | Ruiter et al. |
| 2013/0312138 A1 | 11/2013 | Frohberg et al. |

FOREIGN PATENT DOCUMENTS

| | | | |
|---|---|---|---|
| AU | 749323 B2 | 6/2002 | |
| CA | 1088060 | 10/1980 | |
| CA | 2502981 A1 | 9/2004 | |
| CA | 2521729 A1 | 10/2004 | |
| CA | 2561992 | 3/2007 | |
| CA | 2718396 | 9/2009 | |
| CN | 1840655 A | 10/2006 | |
| DE | 2801429 A1 | 7/1978 | |
| EP | 0054382 A1 | 6/1981 | |
| EP | 0719338 B1 | 6/2003 | |
| EP | 0728213 B1 | 1/2004 | |
| EP | 0663956 B1 | 6/2005 | |
| EP | 0571427 B1 | 10/2006 | |
| EP | 1786908 B1 | 5/2007 | |
| EP | 2039771 | * 3/2009 | |
| EP | 2216408 A1 | 8/2010 | |
| EP | 1999141 B1 | 6/2011 | |
| EP | 1999263 B1 | 4/2013 | |
| JP | 2006304779 | 11/2006 | |
| WO | WO-8910396 A1 | 11/1989 | |
| WO | WO-9102069 A1 | 2/1991 | |
| WO | WO-9205251 A1 | 4/1992 | |
| WO | WO-9214827 A1 | 9/1992 | |
| WO | WO-9318170 A1 | 9/1993 | |
| WO | WO-9404692 A1 | 3/1994 | |
| WO | WO-9404693 A2 | 3/1994 | |
| WO | WO-9409144 A1 | 4/1994 | |
| WO | WO-9411520 A1 | 5/1994 | |
| WO | WO-9421795 A1 | 9/1994 | |
| WO | WO-9423043 A2 | 10/1994 | |
| WO | WO-9504826 A1 | 2/1995 | |
| WO | WO-9507355 A1 | 3/1995 | |
| WO | WO-9509910 A1 | 4/1995 | |
| WO | WO-9509911 A1 | 4/1995 | |
| WO | WO-9513389 A1 | 5/1995 | |
| WO | WO-9520669 A2 | 8/1995 | |
| WO | WO-9526407 A1 | 10/1995 | |
| WO | WO-9531553 A1 | 11/1995 | |
| WO | WO-9535026 A1 | 12/1995 | |
| WO | WO-9601904 A1 | 1/1996 | |
| WO | WO-9615248 A1 | 5/1996 | |
| WO | WO-9619581 A1 | 6/1996 | |
| WO | WO-9621023 A1 | 7/1996 | |
| WO | WO-9626206 A1 | 8/1996 | |
| WO | WO-9627674 A1 | 9/1996 | |
| WO | WO-9630517 A1 | 10/1996 | |
| WO | WO-9630529 A1 | 10/1996 | |
| WO | WO-9633270 A1 | 10/1996 | |
| WO | WO-9634968 A2 | 11/1996 | |
| WO | WO-9638567 A2 | 12/1996 | |
| WO | WO-9704103 A2 | 2/1997 | |
| WO | WO-9711188 A1 | 3/1997 | |
| WO | WO-9713865 A1 | 4/1997 | |
| WO | WO-9720936 A1 | 6/1997 | |
| WO | WO-9726362 A1 | 6/1997 | |
| WO | WO-9730163 A1 | 8/1997 | |
| WO | WO-9732985 A1 | 9/1997 | |
| WO | WO-9741218 A1 | 11/1997 | |
| WO | WO-9742328 A1 | 11/1997 | |
| WO | WO-9744472 A1 | 11/1997 | |
| WO | WO-9745545 A1 | 12/1997 | |
| WO | WO-9746080 A1 | 12/1997 | |
| WO | WO-9747806 A1 | 12/1997 | |
| WO | WO-9747807 A1 | 12/1997 | |
| WO | WO-9747808 A1 | 12/1997 | |
| WO | WO-9800549 A1 | 1/1998 | |
| WO | 9805638 A2 | 2/1998 | |
| WO | WO-9805638 A2 | 2/1998 | |
| WO | WO-9812335 A1 | 3/1998 | |
| WO | WO-9820145 A2 | 5/1998 | |
| WO | WO-9822604 A1 | 5/1998 | |
| WO | WO-9827212 A1 | 6/1998 | |
| WO | WO-9827806 A1 | 7/1998 | |
| WO | WO-9832326 A2 | 7/1998 | |
| WO | WO-9839460 A1 | 9/1998 | |
| WO | WO-9840503 A1 | 9/1998 | |
| WO | WO-9900502 A1 | 1/1999 | |
| WO | WO-9912950 A2 | 3/1999 | |
| WO | WO-9915680 A1 | 4/1999 | |
| WO | WO-9924585 A1 | 5/1999 | |
| WO | WO-9924586 A1 | 5/1999 | |
| WO | WO-9924593 A1 | 5/1999 | |
| WO | WO-9934008 A1 | 7/1999 | |
| WO | WO-9947525 A1 | 9/1999 | |
| WO | WO-9953072 A1 | 10/1999 | |
| WO | WO-9957965 A1 | 11/1999 | |
| WO | WO-9958654 A2 | 11/1999 | |
| WO | WO-9958688 A2 | 11/1999 | |
| WO | WO-9958690 A2 | 11/1999 | |
| WO | WO-9960141 A1 | 11/1999 | |
| WO | WO-9966050 A1 | 12/1999 | |
| WO | WO-0004173 A1 | 1/2000 | |
| WO | WO-0008175 A2 | 2/2000 | |
| WO | WO-0008184 A1 | 2/2000 | |
| WO | WO-0008185 A1 | 2/2000 | |
| WO | WO-0011192 A2 | 3/2000 | |
| WO | WO-0014249 A1 | 3/2000 | |
| WO | WO-0021924 A1 | 4/2000 | |
| WO | WO-0022140 A1 | 4/2000 | |
| WO | WO-0028052 A2 | 5/2000 | |
| WO | WO-0047727 A2 | 8/2000 | |
| WO | WO-0063432 A1 | 10/2000 | |
| WO | WO-0066746 A1 | 11/2000 | |
| WO | WO-0066747 A1 | 11/2000 | |
| WO | WO-0073422 A1 | 12/2000 | |
| WO | WO-0073475 A1 | 12/2000 | |
| WO | WO-0077229 A2 | 12/2000 | |
| WO | WO-0112782 A2 | 2/2001 | |
| WO | WO-0112826 A2 | 2/2001 | |
| WO | WO-0114569 A2 | 3/2001 | |
| WO | WO-0117333 A1 | 3/2001 | |
| WO | WO-0119975 A2 | 3/2001 | |
| WO | WO-0124615 A1 | 4/2001 | |
| WO | WO-0131042 A2 | 5/2001 | |
| WO | WO-0141558 A1 | 6/2001 | |
| WO | WO-0151627 A2 | 7/2001 | |
| WO | WO-0151654 A2 | 7/2001 | |
| WO | WO-0165922 A2 | 9/2001 | |
| WO | WO-0166704 A2 | 9/2001 | |
| WO | WO-0174785 A1 | 10/2001 | |
| WO | WO-0183818 A2 | 11/2001 | |
| WO | WO-0194339 A1 | 12/2001 | |
| WO | WO-0198509 A2 | 12/2001 | |
| WO | WO-0202776 A1 | 1/2002 | |
| WO | WO-0222836 A2 | 3/2002 | |
| WO | WO-0226995 A1 | 4/2002 | |
| WO | WO-0234923 A2 | 5/2002 | |
| WO | WO-0236782 A2 | 5/2002 | |
| WO | WO-0236787 A2 | 5/2002 | |
| WO | WO-0236831 A2 | 5/2002 | |
| WO | WO-0245485 A1 | 6/2002 | |
| WO | WO-02061043 A2 | 8/2002 | |
| WO | WO-02079410 A2 | 10/2002 | |
| WO | WO-02081713 A1 | 10/2002 | |
| WO | WO-02085105 A2 | 10/2002 | |
| WO | WO-02099385 A2 | 12/2002 | |
| WO | WO-02101059 A2 | 12/2002 | |
| WO | WO-03013224 A2 | 2/2003 | |
| WO | WO-03013226 A2 | 2/2003 | |
| WO | WO-03033540 A2 | 4/2003 | |
| WO | WO-03033651 A2 | 4/2003 | |
| WO | WO-03052073 A2 | 6/2003 | |
| WO | WO-03071860 A2 | 9/2003 | |
| WO | WO-03092360 A2 | 11/2003 | |
| WO | 2004007448 A1 | 1/2004 | |
| WO | WO-2004007448 A1 | 1/2004 | |
| WO | WO-2004024928 A2 | 3/2004 | |

(56) References Cited

FOREIGN PATENT DOCUMENTS

| | | |
|---|---|---|
| WO | WO-2004040012 A2 | 5/2004 |
| WO | WO-2004049786 A1 | 6/2004 |
| WO | WO-2004053219 A2 | 6/2004 |
| WO | WO-2004056999 A1 | 7/2004 |
| WO | WO-2004072109 A1 | 8/2004 |
| WO | WO-2004072235 A2 | 8/2004 |
| WO | WO-2004074492 A1 | 9/2004 |
| WO | WO-2004078983 A2 | 9/2004 |
| WO | WO-2004090140 A2 | 10/2004 |
| WO | WO-2004101751 A2 | 11/2004 |
| WO | WO-2004106529 A2 | 12/2004 |
| WO | WO-2004111245 A2 | 12/2004 |
| WO | WO-2004113542 A2 | 12/2004 |
| WO | WO-2005000007 A2 | 1/2005 |
| WO | WO-2005002324 A2 | 1/2005 |
| WO | WO-2005002359 A2 | 1/2005 |
| WO | WO-2005012515 A2 | 2/2005 |
| WO | WO-2005012529 A1 | 2/2005 |
| WO | WO-2005017157 A1 | 2/2005 |
| WO | WO-2005020673 A1 | 3/2005 |
| WO | WO-2005021585 A2 | 3/2005 |
| WO | WO-2005030941 A1 | 4/2005 |
| WO | WO-2005030942 A1 | 4/2005 |
| WO | WO-2005033318 A2 | 4/2005 |
| WO | WO-2005038032 A1 | 4/2005 |
| WO | WO-2005059103 A2 | 6/2005 |
| WO | WO-2005090578 A1 | 9/2005 |
| WO | WO-2005093093 A2 | 10/2005 |
| WO | WO-2005095617 A2 | 10/2005 |
| WO | WO-2005095618 A2 | 10/2005 |
| WO | WO-2005095619 A1 | 10/2005 |
| WO | WO-2005095632 A2 | 10/2005 |
| WO | WO-2005103266 A1 | 11/2005 |
| WO | WO-2005103270 A2 | 11/2005 |
| WO | WO-2005103301 A2 | 11/2005 |
| WO | WO-2005123927 A1 | 12/2005 |
| WO | WO-2006007373 A2 | 1/2006 |
| WO | WO-2006009649 A2 | 1/2006 |
| WO | WO-2006015376 A2 | 2/2006 |
| WO | WO-2006018319 A1 | 2/2006 |
| WO | 2006024411 A2 | 3/2006 |
| WO | WO-2006021972 A1 | 3/2006 |
| WO | WO-2006024351 A1 | 3/2006 |
| WO | WO-2006032469 A2 | 3/2006 |
| WO | WO-2006032538 A1 | 3/2006 |
| WO | WO-2006038794 A2 | 4/2006 |
| WO | WO-2006045633 A1 | 5/2006 |
| WO | WO-2006046861 A2 | 5/2006 |
| WO | WO-2006055851 A2 | 5/2006 |
| WO | WO-2006060634 A2 | 6/2006 |
| WO | WO-2006063862 A1 | 6/2006 |
| WO | WO-2006072603 A2 | 7/2006 |
| WO | WO-2006085966 A2 | 8/2006 |
| WO | WO-2006103107 A1 | 10/2006 |
| WO | WO-2006108674 A2 | 10/2006 |
| WO | WO-2006108675 A2 | 10/2006 |
| WO | WO-2006108702 A1 | 10/2006 |
| WO | WO-2006119457 A1 | 11/2006 |
| WO | WO-2006125065 A2 | 11/2006 |
| WO | WO-2006128568 A2 | 12/2006 |
| WO | WO-2006128569 A2 | 12/2006 |
| WO | WO-2006128570 A1 | 12/2006 |
| WO | WO-2006128571 A2 | 12/2006 |
| WO | WO-2006128572 A1 | 12/2006 |
| WO | WO-2006128573 A2 | 12/2006 |
| WO | WO-2006129204 A2 | 12/2006 |
| WO | WO-2006130436 A2 | 12/2006 |
| WO | WO-2006133827 A2 | 12/2006 |
| WO | WO-2006135717 A1 | 12/2006 |
| WO | WO-2006136351 A2 | 12/2006 |
| WO | WO-2007009823 A1 | 1/2007 |
| WO | WO-2007017186 A1 | 2/2007 |
| WO | WO-2007024782 A2 | 3/2007 |
| WO | WO-2007027777 A2 | 3/2007 |
| WO | WO-2007035650 A2 | 3/2007 |
| WO | WO-2007039314 A2 | 4/2007 |
| WO | WO-2007039315 A1 | 4/2007 |
| WO | WO-2007039316 A1 | 4/2007 |
| WO | WO-2007053015 A2 | 5/2007 |
| WO | 2007068428 A2 | 6/2007 |
| WO | WO-2007068428 A2 | 6/2007 |
| WO | WO-2007073167 A1 | 6/2007 |
| WO | WO-2007076115 A2 | 7/2007 |
| WO | WO-2007080126 A2 | 7/2007 |
| WO | WO-2007080127 A2 | 7/2007 |
| WO | WO-2007091277 A2 | 8/2007 |
| WO | WO-2007092704 A2 | 8/2007 |
| WO | WO-2007103567 A2 | 9/2007 |
| WO | WO-2007103768 A2 | 9/2007 |
| WO | WO-2007107302 A2 | 9/2007 |
| WO | WO-2007107326 A1 | 9/2007 |
| WO | WO-2007131699 A2 | 11/2007 |
| WO | WO-2007140256 A1 | 12/2007 |
| WO | WO-2007142840 A2 | 12/2007 |
| WO | WO-2007146767 A2 | 12/2007 |
| WO | WO-2007146980 A2 | 12/2007 |
| WO | WO-2007147029 A2 | 12/2007 |
| WO | WO-2007147096 A2 | 12/2007 |
| WO | 2008006515 A1 | 1/2008 |
| WO | WO-2008002480 A2 | 1/2008 |
| WO | WO-2008002872 A2 | 1/2008 |
| WO | WO-2008002962 A2 | 1/2008 |
| WO | WO-2008002964 A2 | 1/2008 |
| WO | WO-2008005210 A2 | 1/2008 |
| WO | WO-2008006033 A1 | 1/2008 |
| WO | WO-2008008779 A2 | 1/2008 |
| WO | WO-2008015263 A2 | 2/2008 |
| WO | WO-2008017518 A1 | 2/2008 |
| WO | WO-2008021021 A2 | 2/2008 |
| WO | WO-2008022486 A1 | 2/2008 |
| WO | WO-2008025097 A1 | 3/2008 |
| WO | WO-2008027534 A2 | 3/2008 |
| WO | WO-2008037902 A1 | 4/2008 |
| WO | WO-2008043849 A2 | 4/2008 |
| WO | WO-2008044150 A2 | 4/2008 |
| WO | WO-2008046069 A2 | 4/2008 |
| WO | WO-2008049183 A1 | 5/2008 |
| WO | WO-2008051608 A2 | 5/2008 |
| WO | WO-2008053487 A2 | 5/2008 |
| WO | WO-2008054747 A2 | 5/2008 |
| WO | WO-2008056915 A1 | 5/2008 |
| WO | WO-2008057642 A1 | 5/2008 |
| WO | WO-2008059048 A2 | 5/2008 |
| WO | WO-2008061240 A2 | 5/2008 |
| WO | WO-2008062049 A1 | 5/2008 |
| WO | WO-2008064222 A2 | 5/2008 |
| WO | WO-2008064341 A1 | 5/2008 |
| WO | WO-2008067043 A2 | 6/2008 |
| WO | WO-2008071767 A1 | 6/2008 |
| WO | WO-2008073617 A2 | 6/2008 |
| WO | WO-2008074025 A2 | 6/2008 |
| WO | WO-2008074891 A2 | 6/2008 |
| WO | WO-2008076844 A2 | 6/2008 |
| WO | WO-2008080630 A1 | 7/2008 |
| WO | WO-2008080631 A1 | 7/2008 |
| WO | WO-2008087932 A1 | 7/2008 |
| WO | WO-2008090008 A1 | 7/2008 |
| WO | WO-2008092910 A1 | 8/2008 |
| WO | WO-2008092935 A2 | 8/2008 |
| WO | WO-2008095886 A1 | 8/2008 |
| WO | WO-2008095887 A1 | 8/2008 |
| WO | WO-2008095888 A1 | 8/2008 |
| WO | WO-2008095889 A1 | 8/2008 |
| WO | WO-2008095910 A1 | 8/2008 |
| WO | WO-2008095911 A2 | 8/2008 |
| WO | WO-2008095916 A1 | 8/2008 |
| WO | WO-2008095919 A1 | 8/2008 |
| WO | WO-2008095969 A1 | 8/2008 |
| WO | WO-2008095970 A1 | 8/2008 |
| WO | WO-2008095972 A1 | 8/2008 |
| WO | WO-2008096138 A1 | 8/2008 |
| WO | WO-2008100353 A2 | 8/2008 |
| WO | WO-2008104598 A2 | 9/2008 |
| WO | WO-2008110522 A1 | 9/2008 |

(56) References Cited

FOREIGN PATENT DOCUMENTS

| | | |
|---|---|---|
| WO | WO-2008110848 A2 | 9/2008 |
| WO | WO-2008111779 A1 | 9/2008 |
| WO | WO-2008112019 A2 | 9/2008 |
| WO | WO-2008112613 A2 | 9/2008 |
| WO | WO-2008114282 A2 | 9/2008 |
| WO | WO-2008116829 A1 | 10/2008 |
| WO | WO-2008117537 A1 | 10/2008 |
| WO | WO-2008118394 A1 | 10/2008 |
| WO | WO-2008121320 A2 | 10/2008 |
| WO | WO-2008122406 A1 | 10/2008 |
| WO | WO-2008122980 A2 | 10/2008 |
| WO | WO-2008125245 A1 | 10/2008 |
| WO | WO-2008125983 A2 | 10/2008 |
| WO | WO-2008135206 A2 | 11/2008 |
| WO | WO-2008135467 A2 | 11/2008 |
| WO | WO-2008135603 A2 | 11/2008 |
| WO | WO-2008137108 A2 | 11/2008 |
| WO | WO-2008138975 A1 | 11/2008 |
| WO | WO-2008139334 A2 | 11/2008 |
| WO | WO-2008142034 A2 | 11/2008 |
| WO | WO-2008142036 A2 | 11/2008 |
| WO | WO-2008142146 A1 | 11/2008 |
| WO | WO-2008142163 A2 | 11/2008 |
| WO | WO-2008145629 A2 | 12/2008 |
| WO | WO-2008145675 A2 | 12/2008 |
| WO | WO-2008145761 A1 | 12/2008 |
| WO | WO-2008148872 A1 | 12/2008 |
| WO | WO-2008150165 A1 | 12/2008 |
| WO | WO-2008150473 A2 | 12/2008 |
| WO | WO-2008151780 A1 | 12/2008 |
| WO | WO-2008152008 A2 | 12/2008 |
| WO | WO-2009000736 A2 | 12/2008 |
| WO | WO-2009000789 A1 | 12/2008 |
| WO | WO-2009000848 A1 | 12/2008 |
| WO | WO-2009000876 A1 | 12/2008 |
| WO | 2009007014 A1 | 1/2009 |
| WO | WO-2009003977 A2 | 1/2009 |
| WO | WO-2009007014 A1 | 1/2009 |
| WO | WO-2009009142 A2 | 1/2009 |
| WO | WO-2009010460 A2 | 1/2009 |
| WO | WO-2009012467 A2 | 1/2009 |
| WO | WO-2009013225 A2 | 1/2009 |
| WO | WO-2009013263 A2 | 1/2009 |
| WO | WO-2009014665 A2 | 1/2009 |
| WO | WO-2009015096 A2 | 1/2009 |
| WO | WO-2009016104 A1 | 2/2009 |
| WO | WO-2009016212 A2 | 2/2009 |
| WO | WO-2009016232 A2 | 2/2009 |
| WO | WO-2009016240 A1 | 2/2009 |
| WO | WO-2009021153 A2 | 2/2009 |
| WO | WO-2009021548 A1 | 2/2009 |
| WO | WO-2009031664 A1 | 3/2009 |
| WO | WO-2009034188 A1 | 3/2009 |
| WO | WO-2009036234 A1 | 3/2009 |
| WO | WO-2009037279 A1 | 3/2009 |
| WO | WO-2009037329 A2 | 3/2009 |
| WO | WO-2009037338 A1 | 3/2009 |
| WO | WO-2009038581 A2 | 3/2009 |
| WO | WO-2009040665 A2 | 4/2009 |
| WO | WO-2009049110 A1 | 4/2009 |
| WO | WO-2009052242 A2 | 4/2009 |
| WO | WO-2009053511 A1 | 4/2009 |
| WO | WO-2009054735 A2 | 4/2009 |
| WO | WO-2009056566 A2 | 5/2009 |
| WO | WO-2009060040 A1 | 5/2009 |
| WO | WO-2009061776 A1 | 5/2009 |
| WO | WO-2009064652 A1 | 5/2009 |
| WO | WO-2009065863 A1 | 5/2009 |
| WO | WO-2009065912 A2 | 5/2009 |
| WO | WO-2009067580 A2 | 5/2009 |
| WO | WO-2009068313 A2 | 6/2009 |
| WO | WO-2009068564 A1 | 6/2009 |
| WO | WO-2009068564 A8 | 6/2009 |
| WO | WO-2009068588 A2 | 6/2009 |
| WO | WO-2009072676 A1 | 6/2009 |
| WO | WO-2009073069 A2 | 6/2009 |
| WO | WO-2009073605 A2 | 6/2009 |
| WO | WO-2009075860 A2 | 6/2009 |
| WO | WO-2009077611 A2 | 6/2009 |
| WO | WO-2009077973 A1 | 6/2009 |
| WO | WO-2009079508 A1 | 6/2009 |
| WO | WO-2009079529 A2 | 6/2009 |
| WO | WO-2009080743 A2 | 7/2009 |
| WO | WO-2009080802 A2 | 7/2009 |
| WO | WO-2009083958 A2 | 7/2009 |
| WO | WO-2009086229 A2 | 7/2009 |
| WO | WO-2009086850 A1 | 7/2009 |
| WO | WO-2009091518 A2 | 7/2009 |
| WO | WO-2009091860 A2 | 7/2009 |
| WO | WO-2009092009 A2 | 7/2009 |
| WO | WO-2009092560 A1 | 7/2009 |
| WO | WO-2009092772 A2 | 7/2009 |
| WO | WO-2009094401 A2 | 7/2009 |
| WO | WO-2009094527 A2 | 7/2009 |
| WO | WO-2009095455 A1 | 8/2009 |
| WO | WO-2009095641 A2 | 8/2009 |
| WO | WO-2009095881 A2 | 8/2009 |
| WO | WO-2009097133 A2 | 8/2009 |
| WO | WO-2009099906 A2 | 8/2009 |
| WO | WO-2009102873 A1 | 8/2009 |
| WO | WO-2009102965 A2 | 8/2009 |
| WO | WO-2009102978 A2 | 8/2009 |
| WO | WO-2009105492 A2 | 8/2009 |
| WO | WO-2009105612 A2 | 8/2009 |
| WO | WO-2009106596 A2 | 9/2009 |
| WO | WO-2009108513 A2 | 9/2009 |
| WO | WO-2009111263 A1 | 9/2009 |
| WO | WO-2009111627 A1 | 9/2009 |
| WO | WO-2009112505 A2 | 9/2009 |
| WO | WO-2009113684 A1 | 9/2009 |
| WO | WO-2009114733 A2 | 9/2009 |
| WO | WO-2009117448 A1 | 9/2009 |
| WO | WO-2009117853 A1 | 10/2009 |
| WO | WO-2009126359 A1 | 10/2009 |
| WO | WO-2009126462 A2 | 10/2009 |
| WO | WO-2009127671 A1 | 10/2009 |
| WO | WO-2009129162 A2 | 10/2009 |
| WO | WO-2009132057 A1 | 10/2009 |
| WO | WO-2009132089 A2 | 10/2009 |
| WO | WO-2009132779 A1 | 11/2009 |
| WO | WO-2009132850 A1 | 11/2009 |
| WO | WO-2009134339 A2 | 11/2009 |
| WO | WO-2009135130 A2 | 11/2009 |
| WO | WO-2009135810 A8 | 11/2009 |
| WO | WO-2009141824 A2 | 11/2009 |
| WO | WO-2009143995 A1 | 12/2009 |
| WO | WO-2009145290 A1 | 12/2009 |
| WO | WO-2009148330 A1 | 12/2009 |
| WO | WO-2009149787 A1 | 12/2009 |
| WO | WO-2009150170 A1 | 12/2009 |
| WO | WO-2009150541 A2 | 12/2009 |
| WO | WO-2009153208 A1 | 12/2009 |
| WO | WO-2009156360 A1 | 12/2009 |
| WO | WO-2009158470 A2 | 12/2009 |
| WO | WO-2010000794 A1 | 1/2010 |
| WO | WO-2010003065 A2 | 1/2010 |
| WO | WO-2010003917 A1 | 1/2010 |
| WO | WO-2010005298 A2 | 1/2010 |
| WO | WO-2010006010 A1 | 1/2010 |
| WO | WO-2010006732 A2 | 1/2010 |
| WO | WO-2010007035 A1 | 1/2010 |
| WO | WO-2010007495 A2 | 1/2010 |
| WO | WO-2010007496 A2 | 1/2010 |
| WO | WO-2010012760 A2 | 2/2010 |
| WO | WO-2010012796 A1 | 2/2010 |
| WO | WO-2010019838 A2 | 2/2010 |
| WO | WO-2010019872 A1 | 2/2010 |
| WO | WO-2010023186 A1 | 3/2010 |
| WO | WO-2010023310 A2 | 3/2010 |
| WO | WO-2010023320 A2 | 3/2010 |
| WO | WO-2010024976 A1 | 3/2010 |
| WO | WO-2010025172 A8 | 3/2010 |
| WO | WO-2010025465 A1 | 3/2010 |
| WO | WO-2010025466 A2 | 3/2010 |

(56) References Cited

FOREIGN PATENT DOCUMENTS

| | | |
|---|---|---|
| WO | WO-2010025513 A1 | 3/2010 |
| WO | WO-2010027793 A1 | 3/2010 |
| WO | WO-2010027799 A1 | 3/2010 |
| WO | WO-2010027804 A2 | 3/2010 |
| WO | WO-2010027805 A2 | 3/2010 |
| WO | WO-2010027808 A2 | 3/2010 |
| WO | WO-2010027809 A1 | 3/2010 |
| WO | WO-2010028205 A1 | 3/2010 |
| WO | WO-2010028456 A1 | 3/2010 |
| WO | WO-2010031312 A1 | 3/2010 |
| WO | WO-2010033564 A1 | 3/2010 |
| WO | WO-2010034652 A1 | 4/2010 |
| WO | WO-2010034672 A1 | 4/2010 |
| WO | WO-2010034681 A1 | 4/2010 |
| WO | WO-2010035784 A1 | 4/2010 |
| WO | WO-2010036764 A1 | 4/2010 |
| WO | WO-2010036866 A1 | 4/2010 |
| WO | WO-2010037016 A1 | 4/2010 |
| WO | WO-2010037228 A1 | 4/2010 |
| WO | WO-2010037714 A1 | 4/2010 |
| WO | WO-2010039750 A2 | 4/2010 |
| WO | WO-2011076345 A1 | 6/2011 |

OTHER PUBLICATIONS

Gasser, et al., "Structure, Expression, and Evolution of the 5-Enolpyruvylshikimate-3-phosphate Synthase Genes of Petunia and Tomato", The Journal of Biological Chemistry, 1988, vol. 263, No. 9, pp. 4280-4289.

Crickmore, et al., "Revision of the Nomenclature for the Bacillus thuringiensis Pesticidal Crystal Proteins" Microbiology and Molecular Biology Reviews, Sep. 1998, vol. 62, No. 3, pp. 807-813.

Moellenbeck, et al., "Insecticidal proteins from Bacillus thuringiensis protect corn from corn rootworms", Nature Biotechnology, Jul. 2001, vol. 19, pp. 668-672.

Comai, et al., "An Altered aroA Gene Product Confers Resistance to the Herbicide Blyphosate", Science, vol. 221, 1983, pp. 370-371.

Shah, et al., "Engineering Herbicide Tolerance in Transgenic Plants", Science, vol. 233, 1986, pp. 478-481.

Tranel, et al., "Resistance of weeds to ALS-inhibiting herbicides: what have we learned?", Weed Science, vol. 50, Issue 6, 2002, pp. 700-712.

Colby, S. R., "Calculating Synergistic and Antagonistic Responses of Herbicide Combinations", Weeds, vol. 15, 1967, pp. 20-22.

* cited by examiner

ACTIVE COMPOUND COMBINATIONS COMPRISING SPECIFIC TETRAMIC ACID DERIVATIVES

CROSS REFERENCE TO RELATED APPLICATIONS

This application is a §371 National Stage Application of PCT/EP2012/065469, filed Aug. 7, 2012, which claims priority to 61/521,827, filed Aug. 10, 2011.

BACKGROUND

1. Field of Invention

The invention is in the technical field of crop protection compositions which can be used simultaneously against harmful plants and animal pests such as insects/spider mites, for example in crop plants, and comprise, as active compounds, a combination of at least one insecticide/acaricide and at least one herbicide and, if appropriate, additionally crop plant compatibility-increasing substances (safeners).

2. Description of Related Art

The Co-application of glyphosate plus an insecticide (e.g. Spirotetramat) or fungicides in glyphosate-resistant soybean has been described in Canadian Journal of Plant Science (2012), 92(2), 297-302. Glyphosate tankmixed with e.g. Spirotetramat has no adverse effect on weed control in glyphosate resistant soybean.

WO 98/05638 describes tetramic acid derivatives, their preparation and their use as insecticides/acaricides. The corresponding cis-isomers are described in WO 04/007448.

From WO 07/068428, it is known that the insecticidal/acaricidal activities of tetramic acid derivatives can be improved by adding adjuvants. Also known are the effects of herbicidally active tetramic acid derivatives in combination with other herbicides, for example from WO 06/024411 and WO 09/007014.

The activity of these insecticides/acaricides against animal pests in the crop plants is on a high level; however, it generally depends on the application rate, the formulation in question, the respective animal pests to be controlled, the climatic and soil conditions, etc. A further criterium is the duration of action or the rate of degradation of the insecticide/acaricide. In general, however, there is always a need for methods achieving insecticidal/acaricidal action with a lower active compound application rate. A lower application rate reduces not only the amount of active compound required for application but generally also reduces the amount of formulation auxiliaries required. Both reduce economic expense and improve the ecological compatibility of the insecticide/acaricide treatment.

One way of improving the application profile of an insecticide/acaricide may be to combine the active compound with one or more herbicidally active compounds. However, the combined use of a plurality of active compounds, in particular when insecticides are used together with herbicides, does not infrequently lead to phenomena of physical and biological imcompatibility, for example lacking stability of a coformulation, decomposition of an active compound or antagonism of the active compounds. In contrast, what is desired are combinations of active compounds and/or formulations thereof having a favourable activity profile, high stability and, ideally, synergistically enhanced activity, which permits a reduction of the application rate compared with the individual application of the active compounds to be combined. Likewise advantageous may be a broadening of the activity spectrum, an increased application flexibility and a faster onset of action.

SUMMARY

Surprisingly, it has now been found that certain active compounds from the group of the tetramic acid derivatives in combination with certain structurally different herbicides act together in a particularly favourable manner, for example when used in crop plants suitable for the selective application of the herbicides, which firthermire allow the amount of adjuvants to be reduced and make successive spraying with a herbicide and an insecticide/acaricide unnecessary. This combination offers economical advantages to the user, is ecologically very advantageous and has a positive effect on the water and $CO_2$ balance of the treatment of the crop since one spraying course and thus also the water for preparing the spray liquor is saved, which is advantageous in semiarid regions.

Accordingly, the invention provides combinations of insecticides/acaricides and herbicides comprising an effective amount of components (A) and (B) where
(A) is one or two insecticides/acaricides from group (A) below which consists of the compounds

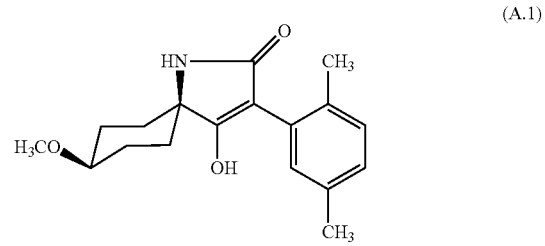

(A.1)

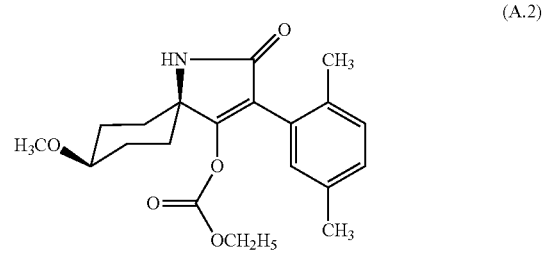

(A.2)

(where A1 is emphasized and A2 is likewise emphasized), and
(B) is one or more herbicides from the list of herbicides and plant growth regulators below:
acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulphamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulphonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorphenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl] methyl}-sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulphate, monolinuron, monosulfuron, monosulfuron esters, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and also the compounds below:

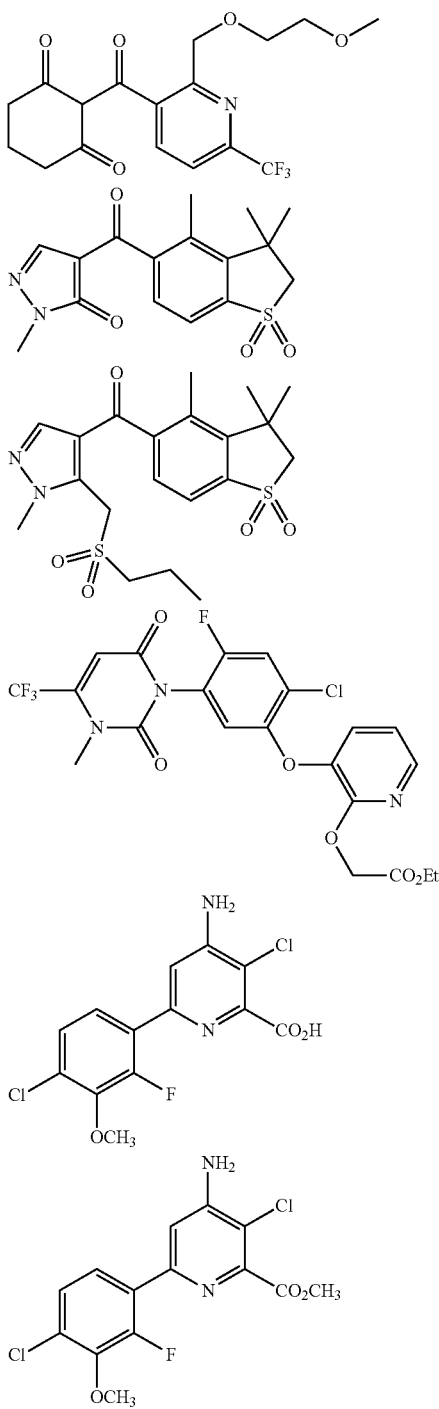

DETAILED DESCRIPTION OF A PREFERRED EMBODIMENT preferably groups (B1) to (B4), group (B-1) comprising herbicides which are predominantly active against monocotyledonous harmful plants, from the group of compounds consisting of (listed by "common name" and a reference, for example "The Pesticide Manual" 13th Ed., British Crop Protection Council 2003, abbreviated "PM")

(B1.1) pinoxaden (WO 99/47525), for example 8-(2,6-diethyl-4-methylphenyl)-1,2,4,5-tetra-hydro-7-oxo-7H-pyrazolo[1,2-d][1,4,5]oxadiazepin-9-yl 2,2-dimethylpropanoate (B1.2) diclofop-methyl (PM, pp. 293-295), for example methyl 2-[4-(2,4-dichlorophenoxy)-phenoxy]propanoate (B1.3) clodinafop-propargyl (PM, pp. 186-187), for example (R)-(2-propynyl) 2-[4-[(5-chloro-3-fluoro-2-pyridinyl)oxy]phenoxy]propanoate (B1.4) cyhalofop-butyl (PM, pp. 229-232), for example (R)-butyl 2-[4-(4-cyano-2-fluorophenoxy)phenoxy]propanoate (B1.5) fenoxaprop-P-ethyl (PM, pp. 414-417), for example (R)-ethyl 2-[4-[(6-chloro-2-benzoxa-zolyl)oxy]phenoxy]propanoate (B1.6) haloxyfop-P (PM, pp. 52-527) and its esters, for example (R)-methyl 2-[4-[[3-chloro-5-(trifluoromethyl)-2-pyridinyl]oxy]phenoxy]propanoate (B1.7) fluazifop-P-butyl (PM, pp. 444-446), for example (R)-butyl 2-[4-[[5-(trifluoromethyl)-2-pyridinyl]oxy]phenoxy]propanoate (B1.8) quizalofop-P (PM, pp. 876-878) and its esters, for example ethyl 2-[4-(6-chloro-2-quin-oxalinyloxy)phenoxy]propanoate (B1.9) sethoxydim (PM, pp. 887-888), for example (+-)-2-[1-(ethoxyimino)butyl]-5-[2-(ethylthio)propyl]-3-hydroxy-2-cyclohexen-1-one (B1.10) clethodim (PM, pp. 185-186), for example (E,E)-(+)-2-[1-[[(3-chloro-2-propenyl)oxy]-imino]propyl]-5-[2-(ethylthio)propyl]-3-hydroxy-2-cyclohexen-1-one (B1.11) tepraloxydim (PM, pp. 936-937), for example 2-[1-[[[(2E)-3-chloro-2-propenyl]oxy]-imino]propyl]-3-hydroxy-5-(tetrahydro-2H-pyran-4-yl)-2-cyclohexen-1-one (B1.12) mesosulfuron-methyl (PM, pp. 630-632), for example methyl 2-[[[[(4, 6-dimethoxy-2-pyrimidinyflamino]carbonyl]amino]sulphonyl]-4-[[(methylsulphonyl)amino]methyl]-benzoate (B1.13) iodosulfuron-methyl and its salts (PM, pp. 573-574), for example methyl 4-iodo-2-[[[[(4-methoxy-6-methyl-1,3,5-triazin-2-yl)amino]carbonyl]amino]sulphonyl]benzoate, monosodium salt (B1.14) sulfosulfuron (PM, pp. 913-915), for example N-[[(4, 6-dimethoxy-2-pyrimidinyl)amino]-carbonyl]-2-(ethylsulphonyl)imidazo[1,2-a]pyridine-3-sulphonamide (B1.15) flupyrsulfuron-methyl and its salts (PM pp. 470-473), for example methyl 2-[[[[(4,6-dimethoxy-2-pyrimidinyl)amino]carbonyl]amino]sulphonyl]-6-(trifluoromethyl)-3-pyridinecarboxylate, monosodium salt (B1.16) fentrazamide (PM, pp. 427-428), for example 4-(2-chlorophenyl)-N-cyclohexyl-N-ethyl-4,5-dihydro-5-oxo-1H-tetrazole-1-carboxamide (B1.17) mefenacet (PM, pp. 621-622), for example 2-(2-benzothiazolyloxy)-N-methyl-N-phenyl-acetamide (B1.18) imazamethabenz-methyl (PM, pp. 551-552), for example methyl 2-[4,5-dihydro-4-methyl-4-(1-methylethyl)-5-oxo-1H-imidazole-2-yl]-4 (or 5)-methylbenzoate (B1.19) imazethapyr (PM, pp. 558-560), for example 2-[4,5-dihydro-4-methyl-4-(1-methylethyl)-5-oxo-1H-imidazol-2-yl]-5-ethyl-3-pyridinecarboxylic acid
(B1.20) imazamox (PM, pp. 552-553), for example 2-[4,5-dihydro-4-methyl-4-(1-methylethyl)-5-oxo-1H-imidazol-2-yl]-5-(methoxymethyl)-3-pyridinecarboxylic acid
(B1.21) flurtamone (PM, pp. 482-483), for example 5-(methylamino)-2-phenyl-4-[3-(trifluoro-methyl)phenyl]-3(2H)-furanone
(B1.22) isoproturon (PM, pp. 584-585), for example N,N-dimethyl-N'-[4-(1-methylethyl)-phenyl]urea
(B1.23) quinclorac (PM, pp. 869-870), for example 3,7-dichloro-8-quinolinecarboxylic acid and
group (B-2) comprising herbicides which are predominantly active against graminaceous and dicotyledonous harmful plants, from the group of compounds consisting of (listed by "common name" and a reference, for example "The Pesticide Manual" 13th Ed., British Crop Protection Council 2003, abbreviated "PM")
(B2.1) 2,4-DB (PM, pp. 264-266) and its esters and salts, for example (2,4-dichlorophenoxy)-acetic acid
(B2.2) dicamba (PM, pp. 278-280) and its esters and salts, for example 3,6-dichloro-2-methoxy-benzoic acid
(B2.3) clomazone (PM, p. 191), for example 2-[(2-chlorophenyl)methyl]-4,4-dimethyl-3-isoxazolidinone
(B2.4) triclopyr (PM, pp. 1001-1002) and its salts and esters, for example [(3,5,6-trichloro-2-pyridinyl)oxy]acetic acid
(B2.5) fluroxypyr and its salts and esters (PM, pp. 478-481), for example 1-methylheptyl-[(4-amino-3,5-dichloro-6-fluoro-2-pyridinyl)oxy]acetate
(B2.6) thifensulfuron-methyl (PM, pp. 963-965), for example methyl 3-[[[[(4-methoxy-6-methyl-1,3,5-triazin-2-yl)amino]carbonyl]amino]sulphonyl]-2-thiophenecarboxylate
(B2.7) amidosulfuron (PM, pp. 27-28), for example N-[[[[(4,6-dimethoxy-2-pyrimidinyl)amino]-carbonyl]amino]sulphonyl]-N-methyl-methanesulphonamide
(B2.8) tribenuron-methyl (PM, pp. 996-998), for example methyl 2-[[[[(4-methoxy-6-methyl-1,3,5-triazin-2-yl)methylamino]carbonyl]amino]sulphonyl]benzoate
(B2.9) metsulfuron-methyl (PM pp. 677-678), for example methyl 2-[[[[(4-methoxy-6-methyl-1,3,5-triazin-2-yl)amino]carbonyl]amino]sulphonyl]benzoate
(B2.10) picloram and its salts and esters (PM pp. 782-785), for example 4-amino-3,5,6-trichloro-2-pyridinecarboxylic acid
(B2.11) carfentrazone-ethyl (PM pp. 143-144), for example ethyl α,2-dichloro-5-[4-(difluoromethyl)-4,5-dihydro-3-methyl-5-oxo-1H-1,2,4-triazol-1-yl]-4-fluorobenzenepropanoate
(B2.12) chlopyralid (PM, pp. 194-195), for example 3,6-dichloro-2-pyridinecarboxylic acid
(B2.13) batafenacil (PM, pp. 120-121), for example 1,1-dimethyl-2-oxo-2-(2-propenyloxy)ethyl 2-chloro-5-[3,6-dihydro-3-methyl-2,6-dioxo-4-(trifluoromethyl)-1(2H)-pyrimidinyl]-benzoate
(B2.14) isoxaben (PM, pp. 587-588), for example N-[3-(1-ethyl-1-methylpropyl)-5-isoxazolyl]-2,6-dimethoxybenzamide
(B2.15) thiazopyr (PM, pp. 961-962), for example methyl 2-(difluoromethyl)-5-(4,5-dihydro-2-thiazolyl)-4-(2-methylpropyl)-6-(trifluoromethyl)-3-pyridinecarboxylate
(B2.16) flurtamone (PM, pp. 482-483), for example 5-(methylamino)-2-phenyl-4-[3-(trifluoromethyl)phenyl]-3(2H)-furanone
(B2.17) aclonifen (PM, p. 13), for example 2-chloro-6-nitro-3-phenoxybenzenamine
(B2.18) lactofen (PM, pp. 596-597), for example 2-ethoxy-1-methyl-2-oxoethyl 5-[2-chloro-4-(trifluoromethyl)phenoxy]-2-nitrobenzoate
(B2.19) fomesafen (PM, pp. 492-493), for example 5-[2-chloro-4-(trifluoromethyl)phenoxy]-N-(methylsulphonyl)-2-nitrobenzamide
(B2.20) chlorimuron-ethyl (PM, pp. 161-162), ethyl 2-[[[[(4-chloro-6-methoxy-2-pyrimidinyl)-amino]carbonyl]amino]sulphonyl]benzoate
(B2.21) mesotrione (PM, pp. 631-632), 2-[4-(methylsulphonyl)-2-nitrobenzoyl]-1,3-cyclohexane-dione
(B2.22) sulcotrione (PM, pp. 908-909), for example 2-[2-chloro-4-(methylsulphonyl)benzoyl]-1,3-cyclohexanedione
(B2.23)

(known form WO 01/74785)

(B2.24)

(known from WO 01/74785)

(B2.25) bromoxynil (PM, pp. 111-113) and its salts and esters, for example 3,5-dibromo-4-hydroxybenzonitrile
(B2.26) ioxynil (PM, pp. 574-576) and its esters and salts, for example 4-hydroxy-3,5-diiodobenzonitrile
(B2.27) diflufenican (PM, pp. 310-311), for example N-(2,4-difluorophenyl)-2-[3-(trifluoromethyl)phenoxy]-3-pyridinecarboxamide
(B2.28) picolinafen (PM, pp. 785-786), for example N-(4-fluorophenyl)-6-[3-(trifluoro-methyl)phenoxy]-2-pyridinecarboxamide
(B2.29) chloransulam (U.S. Pat. No. 5,163,995) and its esters and salts, for example methyl 3-chloro-2-[[(5-ethoxy-7-fluoro[1,2,4]triazolo[1,5-c]pyrimidin-2-yl)-sulphonamino]benzoate
(B2.30) imazaquin (Los, M. et al., Abstr. Pap. 184th ACS Nat. Meet., Kansas City, Sep. 12-17th, 1982, Ref. Pest 21), for example 2-[4,5-dihydro-4-methyl-4-(1-methylethyl)-5-oxo-1H-imidazol-2-yl]-3-quinolinecarboxylic acid
(B2.31) trifloxysulfuron and its salts (S. Howard et al., BCPC-Weeds, 2001, Brighton, Vol. 1, 29-34), for example N-[[(4,6-dimethoxy-2-pyrimidinyl)amino]carbonyl]-3-(2,2,2-trifluoroethoxy)-2-pyridinesulphonamide, monosodium salt and
group (B-3) comprising herbicides which are predominantly active against dicotyledonous harmful plants, from the group of compounds consisting of (listed by "common name" and a reference, for example "The Pesticide Manual" 13th Ed., British Crop Protection Council 2003, abbreviated "PM")

(B3.1) foramsulfuron (PM, pp. 494-495), for example 2-[[[[(4,6-dimethoxy-2-pyrimi-dinyl)amino]carbonyl]amino]sulphonyl]-4-(formylamino)-N,N-dimethylbenzamide (B3.2) iodosulfuron-methyl and its salts (PM, pp. 573-574), for example methyl 4-iodo-2-[[[[(4-methoxy-6-methyl-1,3,5-triazin-2-yl)amino]carbonyl]amino]-sulphonyl]benzoate, monosodium salt (B3.3) sulfosulfuron (PM, pp. 913-915), for example N-[[(4,6-dimethoxy-2-pyrimidinyl)amino]carbonyl]-2-(ethylsulphonyl)imidazo[1,2-a]pyridine-3-sulphonamide (B3.4) amicarbazone (PM, pp. 26-27), for example 4-amino-N-(1,1-dimethylethyl)-4,5-dihydro-3-(1-methylethyl)-5-oxo-1H-1,2,4-triazole-1-carboxamide (B3.5) propoxycarbazone-sodium (PM, pp. 831-832), for example methyl 2-[[[(4,5-dihydro-4-methyl-5-oxo-3-propoxy-1H-1,2,4-triazol-1-yl)carbonyl]amino]-sulphonyl]benzoate, sodium salt (B3.6) flucarbazone-sodium (PM, pp. 447-448), for example 4,5-dihydro-3-methoxy-4-methyl-5-oxo-N-[[2-(trifluoromethoxy)phenyl]sulphonyl]-1H-1,2,4-triazole-1-carboxamide, sodium salt (B3.7) flufenacet (PM, pp. 454-455), for example N-(4-fluorophenyl)-N-(1-methylethyl)-2-[[5-(trifluoromethyl)-1,3,4-thiadiazol-2-yl]oxy]acetamide (B3.8) metribuzin (PM, pp. 675-676), for example 4-amino-6-(1,1-dimethylethyl)-3-(methylthio)-1,2,4-triazin-5(4H)-one (B3.9) triasulfuron (PM, pp. 990-991), for example 2-(2-chloroethoxy)-N-[[(4-methoxy-6-methyl-1,3,5-triazin-2-yl)amino]carbonyl]benzenesulphonamide (B3.10) naproanilide (PM, pp. 695-696), for example 2-(2-naphthalenyloxy)-N-phenyl-propanamide (B3.11) imazapyr (PM, pp. 555-556), for example 2-[4,5-dihydro-4-methyl-4-(1-methylethyl)-5-oxo-1H-imidazol-2-yl]-3-pyridinecarboxylic acid (B3.12) sulfosate (EP-A 54382), for example trimethylsulphonium N-phosphono-methylglycine (B3.13) simazine (PM, pp. 891-892), for example 6-chloro-N,N'-diethyl-1,3,5-triazine-2,4-diamine (B3.14) trifluralin (PM, pp. 1012-1014), for example 2,6-dinitro-N,N-dipropyl-4-(trifluoromethyl)benzenamine (B3.15) pendimethalin (PM, pp. 752-753), for example N-(1-ethylpropyl)-3,4-dimethyl-2,6-dinitrobenzenamine (B3.16) oxadiargyl (PM, pp. 725-726), for example 3-[2,4-dichloro-5-(2-propynyloxy)-phenyl]-5-(1,1-dimethylethyl)-1,3,4-oxadiazol-2(3H)-one (B.3.17) oryzalin (PM, pp. 723-724), for example 4-(dipropylamino)-3,5-dinitrobenzenesulphonamide (B3.18) flazasulfuron (PM, pp. 437-438), for example N-[[(4,6-dimethoxy-2-pyrimidinyl)amino]carbonyl]-3-(trifluoromethyl)-2-pyridinesulphonamide (B3.19) sulfometuron-methyl (PM, pp. 912-913), for example methyl 2-[[[[(4,6-dimethyl-2-pyrimidinyl)amino]carbonyl]amino]sulphonyl]benzoate (B3.20) metazachlor (PM, pp. 641-642), for example 2-chloro-N-(2,6-dimethylphenyl)-N-(1H-pyrazol-1-ylmethyl)acetamide (B3.21) metolachlor (PM, pp. 668-669), 2-chloro-N-(2-ethyl-6-methylphenyl)-N-(2-methoxy-1-methylethyl)acetamide (B3.22) S-metolachlor (PM, pp. 669-670), for example (S)-2-chloro-N-(2-ethyl-6-methylphenyl)-N-(2-methoxy-1-methylethyl)acetamide (B3.23) alachlor (PM, pp. 17-19), for example 2-chloro-N-(2,6-diethylphenyl)-N-(methoxymethyl)acetamide (B3.24) atrazine (PM, pp. 39-41), for example 6-chloro-N-ethyl-N'-(1-methylethyl)-1,3,5-triazine-2,4-diamine (B3.25) isoxaflutole (PM, pp. 589-590), for example (5-cyclopropyl-4-isoxazolyl)[2-(methylsulphonyl)-4-(trifluoromethyl)phenyl]methanone (B3.26) quinmerac (PM, pp. 870-871), for example 7-chloro-3-methyl-8-quinoline-carboxylic acid (B3.27) flumiclorac-pentyl (PM, pp. 460-461), for example pentyl[2-chloro-4-fluoro-5-(1,3,4,5,6,7-hexahydro-1,3-dioxo-2H-isoindol-2-yl)phenoxy]acetate (B3.28) quinclorac (PM pp. 869-870), for example 3,7-dichloro-8-quinolinecarboxylic acid (B3.29)

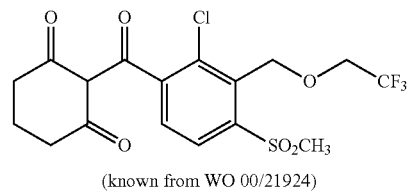 [SMILES: CS(=O)(=O)c1ccc(C(=O)C2C(=O)CCCC2=O)c(Cl)c1COCC(F)(F)F]

(known from WO 00/21924)

(B3.30)

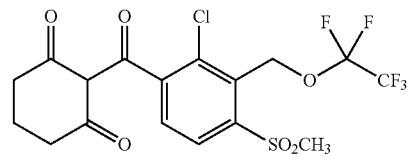

(known from WO 00/21924)

(B3.31)

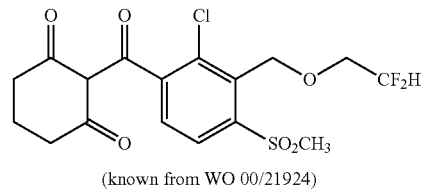 [SMILES: CS(=O)(=O)c1ccc(C(=O)C2C(=O)CCCC2=O)c(Cl)c1COCC(F)F]

(known from WO 00/21924)

(B3.32)

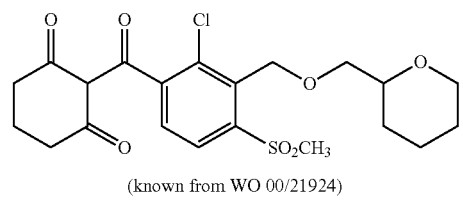 [SMILES: CS(=O)(=O)c1ccc(C(=O)C2C(=O)CCCC2=O)c(Cl)c1COCC1CCCCO1]

(known from WO 00/21924)

(B3.33)

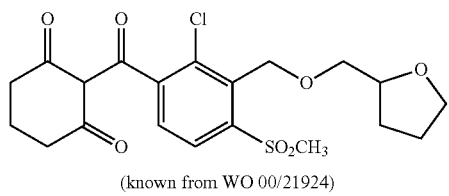 [SMILES: CS(=O)(=O)c1ccc(C(=O)C2C(=O)CCCC2=O)c(Cl)c1COCC1CCCO1]

(known from WO 00/21924)

(B3.34)

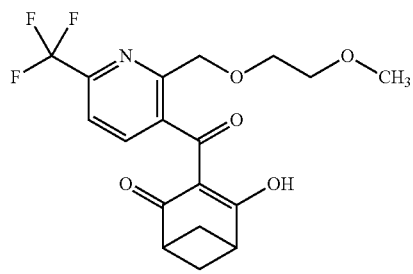

(known from WO 01/094339)

(B3.35)

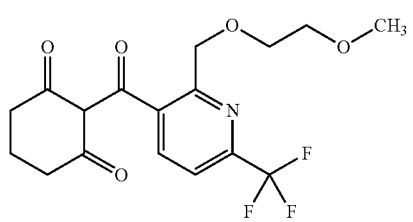

(known from WO 01/094339)

(B3.36)

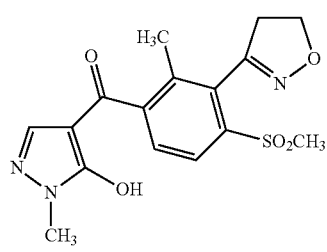

(known from WO 96/26206)

(B3.37) pyrithiobac and its esters and salts (BCPC-Weeds, Brighton, 1991, Vol. 1, 57), for example sodium 2-chloro-6-[(4,6-dimethoxy-2-pyrimidinyl)thio]benzoate and group (B-4) comprising predominantly non-selective herbicides from the group of compounds consisting of (listed by "common name" and a reference, for example "The Pesticide Manual" 13th Ed., British Crop Protection Council 2003, abbreviated "PM")

(B4.1) glyphosate, for example N-(phosphonomethyl)glycine, which is preferably used as glyphosate-isopropylammonium, glyphosate-sesquisodium, glyphosate-trimesium (PM, pp. 513-516)

(B4.2) glufosinate, also comprising glufosinate-P, for example 4-[hydroxy(methyl)-phosphinoyl]-DL-homoalanine, 4-[hydroxy(methyl)phosphinoyl]-L-homoalanine, preferably used as glufosinate-ammonium and glufosinate-P-ammonium, respectively (PM, pp. 511-512)

(B4.3) oxyfluorfen (PM, pp. 738-739), for example 2-chloro-1-(3-ethoxy-4-nitrophenoxy)-4-(trifluoromethyl)benzene (B4.4) diuron (PM, pp. 347-348), for example N'-(3,4-dichlorophenyl)-N,N-dimethylurea (B4.5) MSMA, for example monosodium methylarsonate (B4.6) bromacil (PM, pp. 106-107), for example 5-bromo-6-methyl-3-(1-methylpropyl)-2,4(1H,3H)-pyrimidinedione (B4.7) norflurazon (PM, pp. 711-712), 4-chloro-5-(methylamino)-2 [3-(trifluoromethyl)-phenyl]-3(2H)-pyridazinone (B4.8) azafenidin (DE-A 28 01 429), for example 2-[2,4-dichloro-5-(2-propynyloxy)phenyl]-5,6,7,8-tetrahydro-1,2,4-triazolo[4,3-a]pyridin-3(2H)-one (B4.9) tebuthiuron (PM, pp. 929-930), for example N-[5-(1,1-dimethylethyl)-1,3,4-thiadiazol-2-yl]-N,N'-dimethylurea.

If, in the context of this description, the short form of the "common name" of an active compound is used, this comprises in each case all customary derivatives, such as the esters and salts, and isomers, in particular optical isomers, especially the commercially available form or forms. If the "common name" refers to an ester or a salt, this in each case also comprises all other customary derivatives, such as other esters and salts, the free acids and neutral compounds, and isomers, in particular optical isomers, especially the commercially available form or forms. The given chemical compound names refer to at least one of the compounds embraced by the "common name", frequently to a preferred compound. In the case of sulphonamides such as sulphonylureas, salts also include salts formed by exchanging a hydrogen atom on the sulphonamide group for a cation.

When using the combinations according to the invention of insecticide/acaricide and herbicide, the herbicides of group (B1) are particularly suitable for controlling monocotyledonous harmful plants, the herbicides of group (B2) are particularly suitable for controlling weed grasses and dicotyledonous harmful plants, the herbicides of group (B3) are particularly suitable for controlling dicotyledonous harmful plants and the herbicides of group (B4) are particularly suitable for the non-selective control of harmful plants or of harmful plants in transgenic crops.

The combinations according to the invention of insecticide/acaricide and herbicide comprise an insecticidally/acaricidally effective amount of component (A) and a herbicidally effective amount of component (B) and may comprise further components, for example agrochemically active compounds of a different type and/or additives customary in crop protection and/or formulation auxiliaries, or may be used together with these compounds. Preference is given to combinations of insecticide/acaricide and herbicide comprising a synergistically effective amount of components (A) and (B).

In a preferred embodiment, the combinations according to the invention of insecticide/acaricide and herbicide have synergistic actions. The synergistic actions can be observed, for example, when the commercially available formulations of active compounds (A) and (B) are applied together.

The synergistic effects permit a reduction of the application rates of the insecticidal/acaricidal tetramic acid derivatives, a higher efficacy at the same application rate and/or a reduction in the number of individual applications required and—as a result for the user—an economically and ecologically improved control of animal pests over the period of weed control.

For example, the combinations according to the invention of insecticidally/acaricidally active compounds of group (A) and herbicides (B) allow the activity to be synergistically enhanced in a manner which by far and unexpectedly exceeds the activities which can be achieved with the formulations of the individual active compounds (A) and (B).

The formulae mentioned in groups (A) and (B) include all stereoisomers and their mixtures, in particular also racemic mixtures, and—if enantiomers are possible—the respective biologically active enantiomers.

Compounds of group (A) are described, for example, in the laid-open publications mentioned at the outset.

The compounds of group (B) are known herbicides. The following group members are particularly preferred as mixing partners of the compounds of component (A):

From group (B1): diclofop-methyl (B1.2); fenoxaprop-P-ethyl (B1.5), haloxyfop-P (B1.6), quizalofop-P (B1.8), sethoxydim (B1.9), clethodim (B1.10), imazethapyr (B1.19), imazamox (B1.20).

From group (B2): clomazone (B2.3), lactofen (B2.18), fomesafen (B2.19), bromoxynil (B2.25), ioxynil (B2.26), diflufenican (B2.27), chloransulam (B2.29), imazaquin (B2.30), trifloxysulfuron (B2.31).

From group (B3): pyrithiobac (B3.37).

From group (B4): glyphosate (B4.1), glufosinate (B4.2).

Emphasis is given to glyphosate (B4.1). Emphasis is likewise given to glufosinate (B4.2).

The following combinations are particularly preferred: (A1+B4.1), (A1+B4.2), (A2+B4.1), (A2+B4.2).

Preferred are combinations of insecticide/acaricide and herbicide comprising one or more insecticides/acaricides (A) and one or more herbicides (B), preferably from group (B1) or (B2), (B3) or (B4). More preference is given to combinations of insecticides/acaricides (A) and one or more herbicides (B) according to the scheme: (A)+(B1)+(B2), (A)+(B1)+(B3), (A)+(B1)+(B4), (A)+(B2)+(B3), (A)+(B2)+(B4), (A)+(B3)+(B4).

Very particularly preferred mixtures are:
Backdraft SL (glyphosate+imazaquin)
Canopy EX (tribenzuron+chlorimuron)
Canopy XL (sulfentrazone+chlorimuron)
Extreme (glyphosate+imazapyr)
Flexstar GT (glyphosate+fomesafen)
Fusion (fluazifop+fenoxaprop)
Prefix (fomesafen+S-metolachlor)
Scepter O.T. (imazaquin+acifluorfen)
Select Max (clethodim+glyphosate)
Sequence (glyphosate+S-metolachlor)
Squadron (imazaquin+pendimethalin)
Storm 4S (bentazone+acifluorfen)
Suprend (trifloxysulfuron+prometryn)

In addition, the active compound combinations (mixture) may comprise further fungicidally, acaricidally or insecticidally active additional components.

The application rate of the active compounds of groups (A) and (B) may vary within wide ranges, for example between 0.001 and 8 kg of AS/ha. Whenever the abbreviation AS/ha is used in the present description, this is to be understood as meaning "active substance per hectare", based on 100% pure active compounds.

In the combinations according to the invention between compounds of groups (A) and (B1), the compounds of group (B1) are usually applied at an application rate of from 0.001 to 1.5 kg of AS/ha, preferably 0.005 to 1.2 kg of AS/ha. In the other combinations between compounds of groups (A) and (B), the compounds of group (B) are usually applied at an application rate of from 0.001 to 8 kg of AS/ha, preferably from 0.005 to 5 kg of AS/ha. In the combinations according to the invention, the compound of group (A) or the compounds of group (A) are preferably employed at an application rate of from 1 to 200 g of AS/ha.

The mixing ratio of the compounds of group (A) to those of group (B1) is advantageously from 1:1500 to 120:1, preferably from 1:400 to 18:1. The mixing ratio of the compounds of group (A) to those of group (B2), (B3) or (B4) is advantageously from 1:8000 to 800:1, preferably from 1:100 to 100:1.

When using the active compounds of group (B) in crop plants, it may be expedient, depending on the crop plant, to apply a safener above certain application rates to reduce or avoid possible damage to the crop plant. Such safeners are known to the person skilled in the art. Particularly suitable safeners are benoxacor, cloquintocet, cyprosulfamide, dichlormid, fenclorim, fenchlorazole, furilazole, isoxadifen, mefenpyr, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4). Emphasis is given to cyprosulfamide, isoxadifen, mefenpyr.

The application rates are 1-1000 g of ai/ha, preferably 2-500 g of ai/ha.

If appropriate, the active compound combinations (mixtures) described may comprise a safener. This is also embraced by the invention.

The active compounds can generally be formulated as a water-soluble wettable powder (WP), as water-dispersible granules (WDG), as water-emulsifiable granules (WEG), as a suspoemulsion (SE) or as an oil suspension concentrate (SC).

Application of the combinations according to the invention of insecticide/acaricide and herbicide, if appropriate with the use of a safener, is preferably in annual crops such as, for example, vegetables, melons, ornamental plants, cereals, maize, soya beans, cotton, oilseed rape, potatoes, beet, sugar cane, sunflowers, coffee, tea.

The crops to be protected, which have only been described in a general manner, are described in a more differentiated and more specific manner below. Thus, with respect to the use, vegetable is to be understood as meaning, for example, fruit vegetables and flower-heads as vegetables, for example bell peppers, chilli peppers, tomatoes, aubergines, cucumbers, cucurbits, courgettes, broad beans, runner beans, bush beans, peas, artichokes; but also leafy vegetables, for example lettuce, chicory, endives, cress, rocket salad, field salad, iceberg lettuce, leek, spinach, Swiss chard;

furthermore tuber vegetables, root vegetables and stem vegetables, for example celeriac, beetroot, carrots, garden radish, horseradish, scorzonera, asparagus, table beet, palm shoots, bamboo shoots, moreover bulb vegetables, for example onions, leek, fennel, garlic;

furthermore *brassica* vegetables, such as cauliflowers, broccoli, kohlrabi, red cabbage, white cabbage, green cabbage, Savoy cabbage, Brussels sprouts, Chinese cabbage.

With respect to use, cereal crops are to be understood as meaning, for example, wheat, barley, rye, oats, triticale, but also millet and rice.

The present invention furthermore relates to a method for improving the utilization of the production potential of a transgenic plant, characterized in that the plant is treated with an effective amount of the active compound combinations according to the invention. It is already known that the production potential of a transgenic plant can be enhanced by treatment with the compound of the formula (I) (WO 2009/

132779). This effect is increased by treatment with the active compound combinations according to the invention.

The active compound combinations (mixtures) according to the invention, if appropriate with use of a safener, are suitable for protecting plants and plant organs, for increasing harvest yields, improving the quality of the harvested material and for controlling animal pests, in particular insects, arachnids and nematodes, encountered in agriculture, and they are also tolerated well by plants, have favourable homeotherm toxicity and are tolerated well by the environment. They are preferably used as crop protection compositions. They are active against normally sensitive and resistant species and against all or individual development stages.

The abovementioned pests include in particular:

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., Pentomidae, *Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Meto-polophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

The plant pest nematodes include, for example, *Aphelenchoides* spp., *Bursaphelenchus* spp., *Ditylenchus* spp., *Globodera* spp., *Heterodera* spp., sspp., *Meloidogyne* spp., *Pratylenchus* spp., *Radopholus similis, Trichodorus* spp., *Tylenchulus semipenetrans, Xiphinema* spp.

All plants and plant parts can be treated in accordance with the invention. Plants are understood here to mean all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, preferred examples which may be mentioned being leaves, needles, stems, trunks and flowers.

The treatment according to the invention of the plants and plant parts with the active compound combinations takes place directly or via action on their surroundings or habitat by customary treatment methods, for example by atomizing, spraying, nebulizing, dipping, evaporating, brushing-on and in the case of propagation material, in particular in the case of seeds, furthermore by coating with one or more layers, watering, soil mixing, furrow treatment, droplet application, in hydroponic systems, by planting hole treatment, soil, stem or flower injection, by dip application.

Preferred treatment with the active compound combinations is via foliar application.

As already mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

More preferably, plants of the plant cultivars which are each commercially available or in use are treated in accordance with the invention. Plant cultivars are to be understood as meaning plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processibility of the harvested products, which exceed the effects actually to be expected.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are an improved defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defense of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the improved defense of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal compounds, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance against glyphosate, for example maize, cotton, soya beans), Liberty Link® (tolerance against phosphinothricin, for example oilseed rape), IMI® (tolerance against imidazolinones) and STS (tolerance against sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soya bean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using, for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which imparts particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode-resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a petunia EPSPS (Shah et al., 1986, Science 233, 478-481), a tomato EPSPS (Gasser et al., 1988, J. Biol. Chem. 263, 4280-4289), or an *eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/036782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyses the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585 and WO 99/24586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate dehydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide-resistant plants are plants that are made tolerant to acetolactate synthase (ALS) inhibitors. Known ALS-inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulphonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulphonylurea- and imidazolinone-tolerant plants are also described in for example WO 07/024782 and U.S. Patent Application No. 61/288,958.

Other plants tolerant to imidazolinone and/or sulphonylurea can be obtained by induced mutagenesis, selection in cell cultures in the presence of the herbicide or mutation breeding as described for example for soya beans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 2007/107302), or such proteins encoded by synthetic genes as e.g. described in U.S. patent application Ser. No. 12/249,016; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of two different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or
9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5); or
10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
1) plants which contain a transgene capable of reducing the expression and/or the activity of the poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 and WO 97/20936.

2) transgenic plants which synthesize non-starch carbohydrate polymers or which synthesize non-starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, and plants producing alternan, as disclosed in WO 00/47727, WO 00/73422, EP 06077301.7, U.S. Pat. No. 5,908,975 and EP 0728213.

3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants which contain a mutation imparting such altered fiber characteristics and include:

a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants which contain a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947.
b) Plants such as oilseed rape plants, producing oil having a low linolenic acid content as described in U.S. Pat. Nos. 6,270,828, 6,169,190, or 5,965,755.
c) Plant such as oilseed rape plants, producing oil having a low level of saturated fatty acids as described e.g. in U.S. Pat. No. 5,434,283 or U.S. patent application Ser. No. 12/668,303.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants which contain a mutation imparting such altered seed shattering characteristics and include plants such as oilseed rape plants with delayed or reduced seed shattering as described in U.S. Patent Appl. No. 61/135,230, WO09/068313 and WO10/006732.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested from APHIS.

Additional particularly useful plants containing single transformation events or combinations of transformation events are listed for example in the databases from various national or regional regulatory agencies (see for example http://gmoinfo.jrc.it/gmp_browse.aspx and http://cera-gm-c.org/index.php?evidcode=&hstIDXCode=&gType=&AbbrCode=&atCode=&stCode=&coIDCode=&action=gm_crop_database&mode=Submit).

Further particularly transgenic plants include plants containing a transgene in an agronomically neutral or beneficial position as described in any of the patent publications listed in Table C.

In a particularly preferred variant, the process according to the invention is used to treat transgenic vegetable, cotton and soya bean species.

TABLE A

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
|---|---|---|---|---|
| A-1 | ASR368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061 | *Agrostis stolonifera* Creeping bentgrass |
| A-2 | Asr-368 | | Glyphosate tolerance; US 2006-162007 | bentgrass |
| A-3 | H7-1 | Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*,; WO 2004-074492 | *Beta vulgaris* |
| A-4 | T120-7 | Bayer CropScience (Aventis CropScience (AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Beta vulgaris* |
| A-5 | GTSB77 | Novartis Seeds; Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* (sugar beet) |
| A-6 | T227-1 | | Glyphosate tolerance; US 2004-117870 | *Beta vulgaris* sugar beet |
| A-7 | 23-18-17, 23-198 | Monsanto Company (formerly Calgene) | High laurate (12:0) and myristate (14:0) canola produced by inserting a thioesterase encoding gene from the California bay laurel (*Umbellularia californica*). | *Brassica napus* (Argentine Canola) |
| A-8 | 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. | *Brassica napus* (Argentine Canola) |
| A-9 | 46A12, 46A16 | Pioneer Hi-Bred International Inc. | Combination of chemical mutagenesis, to achieve the high oleic acid trait, and traditional breeding with registered canola varieties. | *Brassica napus* (Argentine Canola) |
| A-10 | GT200 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) |
| A-11 | GT73, RT73 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) |
| A-12 | HCN10 | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| A-13 | HCN92 | Bayer CropScience (Aventis CropScience (AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| A-14 | MS1, RF1 =>PGS1 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| A-15 | MS1, RF2 =>PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) |
| A-16 | MS8×RF3 | Bayer CropScience (Aventis CropScience (AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines | *Brassica napus* (Argentine Canola) |

TABLE A-continued

Non-exhaustive list of transgenic plants and events for working the invention. Source: AgBios database (AGBIOS, P.O. Box 475, 106 St. John St. Merrickville, Ontario K0G1N0, CANADA) which can be accessed under: http://www.agbios.com/dbase.php.

| No. | Transgenic event | Company | Description | Crop |
|---|---|---|---|---|
| A-17 | MS-B2 | | contained the phosphinothricin N-acetyltransferase (PAT) encoding gene from *Streptomyces hygroscopicus*. Male sterility; WO 01/31042 | *Brassica napus* (Argentine Canola) |
| A-18 | MS-BN1/RF-BN1 | | Male sterility/restoration; WO 01/41558 | *Brassica napus* (Argentine Canola) |
| A-19 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | *Brassica napus* (Argentine Canola) |
| A-20 | OXY-235 | Aventis CropScience (formerly Rhone Poulenc Inc.) | Tolerance to the herbicides bromoxynil and ioxynil by incorporation of the nitrilase gene from *Klebsiella pneumoniae*. | *Brassica napus* (Argentine Canola) |
| A-21 | PHY14, PHY35 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) |
| A-22 | PHY36 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT-acetyltransferase (PAT) from *Streptomyces hygroscopicus*. | *Brassica napus* (Argentine Canola) |
| A-23 | RT73 | | Glyphosate resistance; WO 02/36831 | *Brassica napus* (Argentine Canola) |
| A-24 | T45 (HCN28) | Bayer CropScience (Aventis CropScience (AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) |
| A-25 | HCR-1 | Bayer CropScience (Aventis CropScience (AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. | *Brassica rapa* (Polish Canola) |
| A-26 | ZSR500/502 | Monsanto Company | Introduction of a modified 5-enol-pyruvylshikimate-3-phosphate synthase (EPSPS) and a gene from *Achromobacter* sp. that degrades glyphosate by conversion to aminomethylphosphonic acid (AMPA) and glyoxylate by interspecific crossing with GT73. | *Brassica rapa* (Polish Canola) |
| A-27 | EE-1 | | Insect resistance (Cry1Ac); WO 2007/091277 | aubergine |
| A-28 | 55-1/63-1 | Cornell University | Papaya ringspot virus (PRSV) resistant *papaya* produced by inserting the coat protein (CP) encoding sequences from this plant potyvirus. | *Carica papaya* (papaya) |
| A-29 | RM3-3, RM3-4, RM3-6 | Bejo Zaden BV | Male sterility was obtained via insertion of the barnase ribonuclease gene from *Bacillus amyloliquefaciens*; PPT resistance was via the bar gene from *S. hygroscopicus*, which encodes the PAT enzyme. | *Cichorium intybus* (chicory) |
| A-30 | A, B | Agritope Inc. | Reduced accumulation of S-adenosylmethionine (SAM), and consequently reduced ethylene synthesis, by introduction of the gene encoding S-adenosylmethionine hydrolase. | *Cucumis melo* (melon) |
| A-31 | CZW-3 | Asgrow (USA); Seminis Vegetable Inc. (Canada) | Cucumber mosaic virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. | *Cucurbita pepo* (squash) |
| A-32 | ZW20 | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. | *Cucurbita pepo* (squash) |
| A-33 | 66 | Florigene Pty Ltd. | Delayed senescence and sulphonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulphonylurea herbicides was via the | *Dianthus caryophyllus* (carnation) |

TABLE A-continued

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
|---|---|---|---|---|
| A-34 | 4, 11, 15, 16 | Florigene Pty Ltd. | introduction of a chlorsulfuron tolerant version of the acetolactate synthase (ALS) encoding gene from tobacco. Modified colour and sulphonylurea herbicide tolerant carnations produced by inserting two anthocyanin biosynthetic genes whose expression results in a violet/mauve colouration. Tolerance to sulphonylurea herbicides was obtained via the introduction of a chlorsulfuron tolerant version of the acetolactate synthase (ALS) encoding gene from tobacco. | *Dianthus caryophyllus* (carnation) |
| A-35 | 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). | *Dianthus caryophyllus* (carnation) |
| A-36 | 3560.4.3.5 | | Glyphosate/ALS inhibitor-tolerance; WO 2008002872 | *Glycine max* L. (soya bean) |
| A-37 | A2704-12 | | Glufosinate tolerance; WO 2006/108674 | *Glycine max* L. (Soya bean) |
| A-38 | A2704-12, A2704-21, A5547-35 | Aventis CropScience | Glufosinate ammonium herbicide tolerant soya bean produced by inserting a modified phosphinothricin acetyltransferase (PAT) encoding gene from the soil bacterium *Streptomyces viridochromogenes*. | *Glycine max* L. (soya bean) |
| A-39 | A5547-127 | Bayer CropScience (Aventis CropScience (AgrEvo)) | Glufosinate ammonium herbicide tolerant soya bean produced by inserting a modified phosphinothricin acetyltransferase (PAT) encoding gene from the soil bacterium *Streptomyces viridochromogenes*. | *Glycine max* L. (soya bean) |
| A-40 | A5547-35 | | Glufosinate tolerance; WO 2006/108675 | *Glycine max* L. (soya bean) |
| A-41 | DP-305423-1 | | High oleic acid/ALS inhibitor tolerance; WO 2008/054747 | *Glycine max* L. (soya bean) |
| A-42 | DP356043 | Pioneer Hi-Bred International Inc. | Soya bean event with two herbicide tolerance genes: glyphosate N-acetlytransferase, which detoxifies glyphosate, and a modified acetolactate synthase (A | *Glycine max* L. (soya bean) |
| A-43 | G94-1, G94-19, G168 | DuPont Canada Agricultural Products | High oleic acid soya bean produced by inserting a second copy of the fatty acid desaturase (GmFad2-1) encoding gene from soya bean, which resulted in "silencing" of the endogenous host gene. | *Glycine max* L. (soya bean) |
| A-44 | GTS 40-3-2 | Monsanto Company | Glyphosate tolerant soya bean variety produced by inserting a modified 5-enolpyruvylshikimate-3-phosphate synthase (EPSPS) encoding gene from the soil bacterium *Agrobacterium tumefaciens*. | *Glycine max* L. (soya bean) |
| A-45 | GU262 | Bayer CropScience (Aventis CropScience (AgrEvo)) | Glufosinate ammonium herbicide tolerant soya bean produced by inserting a modified phosphinothricin acetyltransferase (PAT) encoding gene from the soil bacterium *Streptomyces viridochromogenes*. | *Glycine max* L. (soya bean) |
| A-46 | MON87701 | | insect resistance (Cry1ac); WO 2009064652 | *Glycine max* L. (soya bean) |
| A-47 | MON87705 | | altered fatty acid levels (mid-oleic and low saturate); WO 2010037016 | *Glycine max* L. (soya bean) |
| A-48 | MON87754 | | increased oil content; WO 2010024976 | *Glycine max* L. (soya bean) |
| A-49 | MON87769 | | stearidonic acid (SDA) comprising oil; WO 2009102873 | *Glycine max* L. (soya bean) |
| A-50 | MON89788 | Monsanto Company | Glyphosate-tolerant soya bean produced by inserting a modified 5-enolpyruvylshikimate-3-phosphate synthase (EPSPS) encoding aroA (epsps) gene from *Agrobacterium tumefaciens* CP4; WO2006130436 | *Glycine max* L. (soya bean) |
| A-51 | OT96-15 | Agriculture & Agri-Food Canada | Low linolenic acid soya bean produced through traditional cross-breeding to incorporate the novel trait from a naturally occurring fan1 gene mutant that was selected for low linolenic acid. | *Glycine max* L. (soya bean) |
| A-52 | W62, W98 | Bayer CropScience (Aventis CropScience (AgrEvo)) | Glufosinate ammonium herbicide tolerant soya bean produced by inserting a modified phosphinothricin acetyltransferase (PAT) encoding gene from the soil bacterium *Streptomyces hygroscopicus*. | *Glycine max* L. (soya bean) |
| A-53 | 15985 | Monsanto Company | Insect resistant cotton derived by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum* L. (cotton) |
| A-54 | 1143-14A | | Insect resistance (Cry1Ab); WO 2006/128569 | *Gossypium hirsutum* L. (cotton) |

TABLE A-continued

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
|---|---|---|---|---|
| A-55 | 1143-51B | | Insect resistance (Cry1Ab); WO 2006/128570 | Gossypium hirsutum L. (cotton) |
| A-56 | 19-51A | DuPont Canada Agricultural Products | Introduction of a variant form of acetolactate synthase (ALS). | Gossypium hirsutum L. (cotton) |
| A-57 | 281-24-236 | DOW AgroSciences LLC | Insect-resistant cotton produced by inserting the cry1F gene from Bacillus thuringiensis var. aizawai. The PAT encoding gene from Streptomyces viridochromogenes was introduced as a selectable marker. | Gossypium hirsutum L. (cotton) |
| A-58 | 3006-210-23 | DOW AgroSciences LLC | Insect-resistant cotton produced by inserting the cry1Ac gene from Bacillus thuringiensis subsp. kurstaki. The PAT encoding gene from Streptomyces viridochromogenes was introduced as a selectable marker. | Gossypium hirsutum L. (cotton) |
| A-59 | 31807/31808 | Calgene Inc. | Insect-resistant and bromoxynil herbicide tolerant cotton produced by inserting the cry1Ac gene from Bacillus thuringiensis and a nitrilase encoding gene from Klebsiella pneumoniae. | Gossypium hirsutum L. (cotton) |
| A-60 | BXN | Calgene Inc. | Bromoxynil herbicide tolerant cotton produced by inserting a nitrilase encoding gene from Klebsiella pneumoniae. | Gossypium hirsutum L. (cotton) |
| A-61 | CE43-67B | | Insect resistance (Cry1Ab); WO 2006/128573 | Gossypium hirsutum L. (cotton) |
| A-62 | CE44-69D | | Insect resistance (Cry1Ab); WO 2006/128571 | Gossypium hirsutum L. (cotton) |
| A-63 | CE46-02A | | Insect resistance (Cry1Ab); WO 2006/128572 | Gossypium hirsutum L. (cotton) |
| A-64 | Cot102 | | Insect resistance (Vip3A); US 2006-130175 | Gossypium hirsutum L. (cotton) |
| A-65 | COT102 | Syngenta Seeds, Inc. | Insect-resistant cotton produced by inserting the vip3A(a) gene from Bacillus thuringiensis AB88. The APH4 encoding gene from E. coli was introduced as a selectable marker. | Gossypium hirsutum L. (cotton) |
| A-66 | COT202 | | Insect resistance (VIP3A); US2009181399 | Gossypium hirsutum L. (cotton) |
| A-67 | Cot202 | | Insect resistance (VIP3); US 2007-067868 | Gossypium hirsutum L. (cotton) |
| A-68 | DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). | Gossypium hirsutum L. (cotton) |
| A-69 | DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). | Gossypium hirsutum L. (cotton) |
| A-70 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). | Gossypium hirsutum L. (cotton) |
| A-71 | EE-GH3 | | Glyphosate tolerance; WO 2007/017186 | Gossypium hirsutum L. (cotton) |
| A-72 | T304-40 | | Insect resistance (Cry1Ab); WO 2008/122406 | Gossypium hirsutum L. (cotton) |
| A-73 | GHB119 | | Insect resistance (cry2Ae); WO2008151780 | Gossypium hirsutum L. (cotton) |
| A-74 | event 281-24-236 | | Insect resistance (Cry1F); WO 2005/103266 | Gossypium hirsutum L. (cotton) |
| A-75 | event3006-210-23 | | Insect resistance (Cry1Ac); WO 2005/103266 | Gossypium hirsutum L. (cotton) |
| A-76 | GHB614 | Bayer CropScience (Aventis CropScience (AgrEvo)) | Glyphosate herbicide tolerant cotton produced by inserting 2MEPSPS gene into variety Coker312 by Agrobacterium under the control of Ph4a748At and TpotpC | Gossypium hirsutum L. (cotton) |
| A-77 | LLCotton25 | Bayer CropScience (Aventis CropScience (AgrEvo)) | Glufosinate ammonium herbicide tolerant cotton produced by inserting a modified phosphinothricin acetyltransferase (PAT) encoding gene from the soil bacterium Streptomyces hygroscopicus; WO 2003013224 | Gossypium hirsutum L. (cotton) |

TABLE A-continued

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
|---|---|---|---|---|
| A-78 | LLCotton25 × MON15985 | Bayer CropScience (Aventis CropScience (AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) | Gossypium hirsutum L. (cotton) |
| A-79 | MON 15985 | | Insect resistance (Cry1A/Cry2Ab); US 2004-250317 | Gossypium hirsutum L. (cotton) |
| A-80 | MON1445/1698 | Monsanto Company | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. | Gossypium hirsutum L. (cotton) |
| A-81 | MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from MON88913 which contains two genes encoding the enzyme 5-enolypyruvylshikimate-3-phosphate synthase (EPSPS) from the CP4 strain of *Agrobacterium tumefaciens*. Insect resistance is derived from the line MON15985 which was produced by transformation of the DP50B parent variety, which contained event 531 (expressing Cry1Ac protein), with purified plasmid DNA containing the cry2Ab gene from *B. thuringiensis* subsp. *kurstaki*. | Gossypium hirsutum L. (cotton) |
| A-82 | MON-15985-7 × MON-Ø1445-2 | Monsanto Company | Stacked insect resistant and herbicide tolerant cotton derived from conventional cross-breeding of the parental lines 15985 (OECD identifier: MON-15985-7) and MON1445 (OECD identifier: MON-Ø1445-2). | Gossypium hirsutum L. (cotton) |
| A-83 | MON531/757/1076 | Monsanto Company | Insect-resistant cotton produced by inserting the cry1Ac gene from *Bacillus thuringiensis* subsp. kurstaki HD-73 (B.t.k.). | Gossypium hirsutum L. (cotton) |
| A-84 | MON88913 | Monsanto Company | Glyphosate herbicide tolerant cotton produced by inserting two genes encoding the enzyme 5-enolypyruvylshikimate-3-phosphate synthase (EPSPS) from the CP4 strain of *Agrobacterium tumefaciens*; WO 2004/072235 | Gossypium hirsutum L. (cotton) |
| A-85 | MON-ØØ531-6 × MON-Ø1445-2 | Monsanto Company | Stacked insect resistant and herbicide tolerant cotton derived from conventional cross-breeding of the parental lines MON531 (OECD identifier: MON-ØØ531-6) and MON1445 (OECD identifier: MON-Ø1445-2). | Gossypium hirsutum L. (cotton) |
| A-86 | PV-GHGT07 (1445) | | Glyphosate tolerance; US 2004-148666 | Gossypium hirsutum L. (cotton) |
| A-87 | T304-40 | | Insect-resistance (Cry1Ab); WO2008/122406 | Gossypium hirsutum L. (cotton) |
| A-88 | T342-142 | | Insect resistance (Cry1Ab); WO 2006/128568 | Gossypium hirsutum L. (cotton) |
| A-89 | X81359 | BASF Inc. | Tolerance to imidazolinone herbicides by selection of a naturally occurring mutant. | Helianthus annuus (sunflower) |
| A-90 | RH44 | BASF Inc. | Selection for a mutagenized version of the enzyme acetohydroxyacid synthase (AHAS), also known as acetolactate synthase (ALS) or acetolactate pyruvate lyase. | Lens culinaris (lentil) |
| A-91 | FP967 | University of Saskatchewan, Crop Dev. Centre | A variant form of acetolactate synthase (ALS) was obtained from a chlorsulfuron tolerant line of *A. thaliana* and used to transform flax. | Linum usitatissimum L. (flax, linseed) |
| A-92 | 5345 | Monsanto Company | Resistance to lepidopteran pests through the introduction of the cry1Ac gene from *Bacillus thuringiensis* subsp. *Kurstaki*. | Lycopersicon esculentum (tomato) |
| A-93 | 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. | Lycopersicon esculentum (tomato) |
| A-94 | 1345-4 | DNA Plant Technology Corporation | Delayed ripening tomatoes produced by inserting an additional copy of a truncated gene encoding 1-aminocyclopropane-1-carboxyllic acid (ACC) synthase, which resulted in downregulation of the endogenous ACC synthase and reduced ethylene accumulation. | Lycopersicon esculentum (tomato) |
| A-95 | 35 1 N | Agritope Inc. | Introduction of a gene sequence encoding the enzyme S-adenosylmethionine hydrolase that metabolizes the precursor of the fruit ripening hormone ethylene | Lycopersicon esculentum (tomato) |
| A-96 | B, Da, F | Zeneca Seeds | Delayed softening tomatoes produced by inserting a truncated version of the polygalacturonase (PG) encoding gene in the sense or anti-sense orientation | Lycopersicon esculentum (tomato) |

TABLE A-continued

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
|---|---|---|---|---|
| A-97 | FLAVR SAVR | Calgene Inc. | in order to reduce expression of the endogenous PG gene, and thus reduce pectin degradation. Delayed softening tomatoes produced by inserting an additional copy of the polygalacturonase (PG) encoding gene in the anti-sense orientation in order to reduce expression of the endogenous PG gene and thus reduce pectin degradation. | *Lycopersicon esculentum* (tomato) |
| A-98 | J101, J163 | Monsanto Company and Forage Genetics International | Glyphosate herbicide tolerant alfalfa (lucerne) produced by inserting a gene encoding the enzyme 5-enolpyruvylshikimate-3-phosphate synthase (EPSPS) from the CP4 strain of *Agrobacterium tumefaciens*. | *Medicago sativa* (alfalfa) |
| A-99 | C/F/93/08-02 | Societe National d'Exploitation des Tabacs et Allumettes | Tolerance to the herbicides bromoxynil and ioxynil by incorporation of the nitrilase gene from *Klebsiella pneumoniae*. | *Nicotiana tabacum* L. (tobacco) |
| A-100 | Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. | *Nicotiana tabacum* L. (tobacco) |
| A-101 | CL121, CL141, CFX51 | BASF Inc. | Tolerance to the imidazolinone herbicide, imazethapyr, induced by chemical mutagenesis of the acetolactate synthase (ALS) enzyme using ethyl methanesulphonate (EMS). | *Oryza sativa* (rice) |
| A-102 | GAT-OS2 | | Glufosinate tolerance; WO 01/83818 | *Oryza sativa* (rice) |
| A-103 | GAT-OS3 | | Glufosinate tolerance; US 2008-289060 | *Oryza sativa* (rice) |
| A-104 | IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (rice) |
| A-105 | LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). | *Oryza sativa* (rice) |
| A-106 | LLRICE601 | Bayer CropScience (Aventis CropScience (AgrEvo)) | Glufosinate ammonium herbicide tolerant rice produced by inserting a modified phosphinothricin acetyltransferase (PAT) encoding gene from the soil bacterium *Streptomyces hygroscopicus*). | *Oryza sativa* (rice) |
| A-107 | PE-7 | | Insect resistance (Cry1Ac); WO 2008/114282 | *Oryza sativa* (rice) |
| A-108 | PWC16 | BASF Inc. | Tolerance to the imidazolinone herbicide, imazethapyr, induced by chemical mutagenesis of the acetolactate synthase (ALS) enzyme using ethyl methanesulphonate (EMS). | *Oryza sativa* (rice) |
| A-109 | TT51 | | Insect resistance (Cry1Ab/Cry1Ac); CN1840655 | *Oryza sativa* (rice) |
| A-110 | C5 | United States Department of Agriculture - Agricultural Research Service | Plum pox virus (PPV) resistant plum tree produced through *Agrobacterium*-mediated transformation with a coat protein (CP) gene from the virus. | *Prunus domestica* (plum) |
| | EH92-527 | BASF Plant Science | Crop composition; Amflora; Unique EU identifier: BPS-25271-9 | |
| A-111 | ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *tenebrionis*). | *Solanum tuberosum* L. (potato) |
| A-112 | BT6, BT10, BT12, BT16, BT17, BT18, BT23 | Monsanto Company | Colorado potato beetle resistant potatoes produced by inserting the cry3A gene from *Bacillus thuringiensis* (subsp. *tenebrionis*). | *Solanum tuberosum* L. (potato) |
| A-113 | RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. *tenebrionis*) and the coat protein encoding gene from PVY. | *Solanum tuberosum* L. (potato) |
| A-114 | RBMT21-129, RBMT21-350, RBMT22-082 | Monsanto Company | Colorado potato beetle and potato leafroll virus (PLRV) resistant potatoes produced by inserting the cry3A gene from *Bacillus thuringiensis* (subsp. *tenebrionis*) and the replicase encoding gene from PLRV. | *Solanum tuberosum* L. (potato) |

TABLE A-continued

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
| --- | --- | --- | --- | --- |
| A-115 | AP205CL | BASF Inc. | Selection for a mutagenized version of the enzyme acetohydroxyacid synthase (AHAS), also known as acetolactate synthase (ALS) or acetolactate pyruvate lyase. | Triticum aestivum (wheat) |
| A-116 | AP602CL | BASF Inc. | Selection for a mutagenized version of the enzyme acetohydroxyacid synthase (AHAS), also known as acetolactate synthase (ALS) or acetolactate pyruvate lyase. | Triticum aestivum (wheat) |
| A-117 | BW255-2, BW238-3 | BASF Inc. | Selection for a mutagenized version of the enzyme acetohydroxyacid synthase (AHAS), also known as acetolactate synthase (ALS) or acetolactate pyruvate lyase. | Triticum aestivum (wheat) |
| A-118 | BW7 | BASF Inc. | Tolerance to imidazolinone herbicides induced by chemical mutagenesis of the acetohydroxyacid synthase (AHAS) gene using sodium azide. | Triticum aestivum (wheat) |
| A-119 | Event 1 | | Fusarium resistance (trichothecene 3-O-acetyltransferase); CA 2561992 | Triticum aestivum (wheat) |
| A-120 | JOPLIN1 | | disease (fungal) resistance (trichothecene 3-O-acetyltransferase); US 2008064032 | Triticum aestivum (wheat) |
| A-121 | MON71800 | Monsanto Company | Glyphosate tolerant wheat variety produced by inserting a modified 5-enolpyruvylshikimate-3-phosphate synthase (EPSPS) encoding gene from the soil bacterium Agrobacterium tumefaciens, strain CP4. | Triticum aestivum (wheat) |
| A-122 | SWP965001 | Cyanamid Crop Protection | Selection for a mutagenized version of the enzyme acetohydroxyacid synthase (AHAS), also known as acetolactate synthase (ALS) or acetolactate pyruvate lyase. | Triticum aestivum (wheat) |
| A-123 | Teal 11A | BASF Inc. | Selection for a mutagenized version of the enzyme acetohydroxyacid synthase (AHAS), also known as acetolactate synthase (ALS) or acetolactate pyruvate lyase. | Triticum aestivum (wheat) |
| A-124 | 176 | Syngenta Seeds, Inc. | Insect-resistant maize produced by inserting the cry1Ab gene from Bacillus thuringiensis subsp. kurstaki. The genetic modification affords resistance to attack by the European corn borer (ECB). | Zea mays L. (maize) |
| A-125 | 3272 | | Self processing corn (alpha-amylase); US 2006-230473 | Zea mays L. (maize) |
| A-126 | 3751IR | Pioneer Hi-Bred International Inc. | Selection of somaclonal variants by culture of embryos on imidazolinone containing media. | Zea mays L. (maize) |
| A-127 | 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from Escherichia coli and Streptomyces viridochromogenes, respectively. | Zea mays L. (maize) |
| A-128 | ACS-ZMØØ3-2 × MON-ØØ81Ø-6 | Bayer CropScience (Aventis CropScience (AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). | Zea mays L. (maize) |
| A-129 | B16 | | Glufosinate resistance; US 2003-126634 | Zea mays L. (maize) |
| A-130 | B16 (DLL25) | Dekalb Genetics Corporation | Glufosinate ammonium herbicide tolerant maize produced by inserting the gene encoding phosphinothricin acetyltransferase (PAT) from Streptomyces hygroscopicus. | Zea mays L. (maize) |
| A-131 | BT11 (X4334CBR, X4734CBR) | Syngenta Seeds, Inc. | Insect-resistant and herbicide tolerant maize produced by inserting the cry1Ab gene from Bacillus thuringiensis subsp. kurstaki, and the phosphinothricin N-acetyltransferase (PAT) encoding gene from S. viridochromogenes. | Zea mays L. (maize) |
| A-132 | BT11 × MIR604 | Syngenta Seeds, Inc. | Stacked insect resistant and herbicide tolerant maize produced by conventional cross breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from Bacillus thuringiensis subsp. kurstaki, and the phosphinothricin N-acetyltransferase (PAT) encoding gene from S. viridochromogenes. Corn rootworm-resistance is derived from MIR604 which contains the mcry3A gene from Bacillus thuringiensis. | Zea mays L. (maize) |
| A-133 | BT11 × MIR604 × GA21 | Syngenta Seeds, Inc. | Stacked insect resistant and herbicide tolerant maize produced by conventional cross breeding of parental lines BT11 (OECD unique identifier: SYN-BTØ11-1), MIR604 (OECD unique identifier: SYN-IR6Ø5-5) and GA21 (OECD unique identifier: MON-ØØØ21-9). Resistance to the European Corn Borer | Zea mays L. (maize) |

TABLE A-continued

Non-exhaustive list of transgenic plants and events for working the invention. Source: AgBios database (AGBIOS, P.O. Box 475, 106 St. John St. Merrickville, Ontario K0G1N0, CANADA) which can be accessed under: http://www.agbios.com/dbase.php.

| No. | Transgenic event | Company | Description | Crop |
|---|---|---|---|---|
| | | | and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. Tolerance to glyphosate herbcicide is derived from GA21 which contains a a modified EPSPS gene from maize. | |
| A-134 | CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. | *Zea mays* L. (maize) |
| A-135 | DAS-06275-8 | DOW AgroSciences LLC | Lepidopteran insect resistant and glufosinate ammonium herbicide-tolerant maize variety produced by inserting the cry1F gene from *Bacillus thuringiensis* var *aizawai* and the phosphinothricin acetyltransferase (PAT) from *Streptomyces hygroscopicus*. | *Zea mays* L. (maize) |
| A-136 | DAS-59122-7 | DOW AgroSciences LLC and Pioneer Hi-Bred International Inc. | Corn rootworm-resistant maize produced by inserting the cry34Ab1 and cry35Ab1 genes from *Bacillus thuringiensis* strain PS149B1. The PAT encoding gene from *Streptomyces viridochromogenes* was introduced as a selectable marker; US 2006-070139 | *Zea mays* L. (maize) |
| A-137 | DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Tolerance to glyphosate herbcicide is derived from NK603. | *Zea mays* L. (maize) |
| A-138 | DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Lepidopteran resistance and toleraance to glufosinate ammonium herbicide is derived from TC1507. Tolerance to glyphosate herbcicide is derived from NK603. | *Zea mays* L. (maize) |
| A-139 | DAS-Ø15Ø7-1 × MON-ØØ6Ø3-6 | DOW AgroSciences LLC | Stacked insect resistant and herbicide tolerant maize derived from conventional cross-breeding of the parental lines 1507 (OECD identifier: DAS-Ø15Ø7-1) and NK603 (OECD identifier: MON-ØØ6Ø3-6). | *Zea mays* L. (maize) |
| A-140 | DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* | *Zea mays* L. (maize) |
| A-141 | DK404SR | BASF Inc. | Somaclonal variants with a modified acetyl-CoA-carboxylase (ACCase) were selected by culture of embryos on sethoxydim enriched medium. | *Zea mays* L. (maize) |
| A-142 | DP-098140-6 | | Glyphosate tolerance/ALS inhibitor tolerance; WO 2008/112019 | *Zea mays* L. (maize) |
| A-143 | DP-Ø9814Ø-6 (Event 98140) | Pioneer Hi-Bred International Inc. | Corn line 98140 was genetically engineered to express the GAT4621 (glyphosate acetyltransferase) and ZM-HRA (modified version of a maize acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. | *Zea mays* L. (maize) |
| A-144 | Event 3272 | Syngenta Seeds, Inc. | Maize line expressing a heat stable alpha-amylase gene amy797E for use in the dry-grind ethanol | *Zea mays* L. (maize) |

TABLE A-continued

Non-exhaustive list of transgenic plants and events for working the invention. Source: AgBios database (AGBIOS, P.O. Box 475, 106 St. John St. Merrickville, Ontario K0G1N0, CANADA) which can be accessed under: http://www.agbios.com/dbase.php.

| No. | Transgenic event | Company | Description | Crop |
|---|---|---|---|---|
| A-145 | EXP1910IT | Syngenta Seeds, Inc. (formerly Zeneca Seeds) | production process. The phosphomannose isomerase gene from *E. coli* was used as a selectable marker. Tolerance to the imidazolinone herbicide, imazethapyr, induced by chemical mutagenesis of the acetolactate synthase (ALS) enzyme using ethyl methanesulphonate (EMS). | *Zea mays* L. (maize) |
| A-146 | FI117 | | Glyphosate resistance; U.S. Pat. No. 6,040,497 | *Zea mays* L. (maize) |
| A-147 | GA21 | Monsanto Company | Induction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (maize) |
| A-148 | GAT-ZM1 | | Glufosinate tolerance; WO 01/51654 | *Zea mays* L. (maize) |
| A-149 | GG25 | | Glyphosate resistance; U.S. Pat. No. 6,040,497 | *Zea mays* L. (maize) |
| A-150 | GJ11 | | Glyphosate resistance; U.S. Pat. No. 6,040,497 | *Zea mays* L. (maize) |
| A-151 | IT | Pioneer Hi Bred International Inc. | Tolerance to the imidazolinone herbicide, imazethapyr, was obtained by in vitro selection of somaclonal variants. | *Zea mays* L. (maize) |
| A-152 | LY038 | Monsanto Company | Altered amino acid composition, specifically elevated levels of lysine, through the introduction of the cordapA gene, derived from *Corynebacterium glutamicum*, encoding the enzyme dihydrodipicolinate synthase (cDHDPS); U.S. Pat. No. 7,157,281 | *Zea mays* L. (maize) |
| A-153 | MIR162 | | Insect resistance; WO 2007142840 | *Zea mays* L. (maize) |
| A-154 | MIR604 | Syngenta Seeds, Inc. | Corn rootworm resistant maize produced by transformation with a modified cry3A gene. The phosphomannose isomerase gene from E. coli was used as a selectable marker; (Cry3a055); EP 1 737 290 | *Zea mays* L. (maize) |
| A-155 | MIR604 × GA21 | Syngenta Seeds, Inc. | Stacked insect resistant and herbicide tolerant maize produced by conventional cross breeding of parental lines MIR604 (OECD unique identifier: SYN-IR6Ø5-5) and GA21 (OECD unique identifier: MON-ØØØ21-9). Corn rootworm-resistance is derived from MIR604 which contains the mcry3A gene from *Bacillus thuringiensis*. Tolerance to glyphosate herbcicide is derived from GA21. | *Zea mays* L. (maize) |
| A-156 | MON80100 | Monsanto Company | Insect-resistant maize produced by inserting the cry1Ab gene from *Bacillus thuringiensis* subsp. *kurstaki*. The genetic modification affords resistance to attack by the European corn borer (ECB). | *Zea mays* L. (maize) |
| A-157 | MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. | *Zea mays* L. (maize) |
| A-158 | MON809 | Pioneer Hi-Bred International Inc. | Resistance to European corn borer (*Ostrinia nubilalis*) by introduction of a synthetic cry1Ab gene. Glyphosate resistance via introduction of the bacterial version of a plant enzyme, 5-enolpyruvyl shikimate-3-phosphate synthase (EPSPS). | *Zea mays* L. (maize) |
| A-159 | MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB); US 2004-180373 | *Zea mays* L. (maize) |
| A-160 | MON810 × MON88017 | Monsanto Company | Stacked insect resistant and glyphosate tolerant maize derived from conventional cross-breeding of the parental lines MON810 (OECD identifier: MON-ØØ81Ø-6) and MON88017 (OECD identifier: MON-88Ø17-3). European corn borer (ECB) resistance is derived from a truncated form of the cry1Ab gene from *Bacillus thuringiensis* subsp. *kurstaki* HD-1 present in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. | *Zea mays* L. (maize) |
| A-161 | MON832 | Monsanto Company | Introduction, by particle bombardment, of glyphosate oxidase (GOX) and a modified 5-enolpyruvyl shikimate-3-phosphate synthase | *Zea mays* L. (maize) |

TABLE A-continued

Non-exhaustive list of transgenic plants and events for working the invention. Source: AgBios database (AGBIOS, P.O. Box 475, 106 St. John St. Merrickville, Ontario K0G1N0, CANADA) which can be accessed under: http://www.agbios.com/dbase.php.

| No. | Transgenic event | Company | Description | Crop |
|---|---|---|---|---|
| | | | (EPSPS), an enzyme involved in the shikimate biochemical pathway for the production of the aromatic amino acids. | |
| A-162 | MON863 | Monsanto Company | Corn root worm resistant maize produced by inserting the cry3Bb1 gene from *Bacillus thuringiensis* subsp. *kumamotoensis*. | *Zea mays* L. (maize) |
| A-163 | MON87460 | | Drought tolerance; water deficit tolerance; WO 2009/111263 | *Zea mays* L. (maize) |
| A-164 | MON88017 | Monsanto Company | Corn rootworm-resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4; WO2005059103 | *Zea mays* L. (maize) |
| A-165 | MON89034 | Monsanto Company | Maize event expressing two different insecticidal proteins from *Bacillus thuringiensis* providing resistance to a number of lepidopteran pests; insect resistance (Lepidoptera-Cry1A.105-Cry2Ab); WO 2007140256 | *Zea mays* L. (maize) |
| A-166 | MON89034 × MON88017 | Monsanto Company | Stacked insect resistant and glyphosate tolerant maize derived from conventional cross-breeding of the parental lines MON89034 (OECD identifier: MON-89Ø34-3) and MON88017 (OECD identifier: MON-88Ø17-3). Resistance to Lepiopteran insects is derived from two crygenes present in MON89043. Corn rootworm resistance is derived from a single cry gene and glyphosate tolerance is derived from the 5-enolpyruvylshikimate-3-phosphate synthase (EPSPS) encoding gene from *Agrobacterium tumefaciens* present in MON88017. | *Zea mays* L. (maize) |
| A-167 | MON-ØØ6Ø3-6 × MON-ØØ81Ø-6 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). | *Zea mays* L. (maize) |
| A-168 | MON-ØØ81Ø-6 × LY038 | Monsanto Company | Stacked insect resistant and enhanced lysine content maize derived from conventional cross-breeding of the parental lines MON810 (OECD identifier: MON-ØØ81Ø-6) and LY038 (OECD identifier: REN-ØØØ38-3). | *Zea mays* L. (maize) |
| A-169 | MON-ØØ863-5 × MON-ØØ6Ø3-6 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). | *Zea mays* L. (maize) |
| A-170 | MON-ØØ863-5 × MON-ØØ81Ø-6 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) | *Zea mays* L. (maize) |
| A-171 | MON-ØØ863-5 × MON-ØØ81Ø-6 × MON-ØØ6Ø3-6 | Monsanto Company | Stacked insect resistant and herbicide tolerant corn hybrid derived from conventional cross-breeding of the stacked hybrids MON-ØØ863-5 × MON-ØØ81Ø-6 and NK603 (OECD identifier: MON-ØØ6Ø3-6). | *Zea mays* L. (maize) |
| A-172 | MON-ØØØ21-9 × MON-ØØ81Ø-6 | Monsanto Company | Stacked insect resistant and herbicide tolerant corn hybrid derived from conventional cross-breeding of the parental lines GA21 (OECD identifder: MON-ØØØ21-9) and MON810 (OECD identifier: MON-ØØ81Ø-6). | *Zea mays* L. (maize) |
| A-173 | MS3 | Bayer CropScience (Aventis CropScience (AgrEvo)) | Male sterility caused by expression of the barnase ribonuclease gene from *Bacillus amyloliquefaciens*; PPT resistance was via PPT-acetyltransferase (PAT). | *Zea mays* L. (maize) |
| A-174 | MS6 | Bayer CropScience (Aventis CropScience (AgrEvo)) | Male sterility caused by expression of the barnase ribonuclease gene from *Bacillus amyloliquefaciens*; PPT resistance was via PPT-acetyltransferase (PAT). | *Zea mays* L. (maize) |
| A-175 | NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (maize) |
| A-176 | PV-ZMGT32 (NK603) | | Glyphosate tolerance; US 2007-056056 | *Zea mays* L. (maize) |
| A-177 | PV-ZMGT32(nk603) | | Glyphosate tolerance; US 2007292854 | *Zea mays* L. (maize) |

TABLE A-continued

Non-exhaustive list of transgenic plants and events for working the invention. Source:
AgBios database (AGBIOS, P.O. Box 475, 106 St. John St. Merrickville, Ontario K0G1N0,
CANADA) which can be accessed under: http://www.agbios.com/dbase.php.

| No. | Transgenic event | Company | Description | Crop |
|---|---|---|---|---|
| A-178 | PV-ZMIR13 (MON863) | | Insect resistance (Cry3Bb); US 2006-095986 | Zea mays L. (maize) |
| A-179 | SYN-BTØ11-1 × MON-ØØØ21-9 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). | Zea mays L. (maize) |
| A-180 | T14, T25 | Bayer CropScience (Aventis CropScience (AgrEvo)) | Glufosinate herbicide tolerant maize produced by inserting the phosphinothricin N-acetyltransferase (PAT) encoding gene from the aerobic actinomycete Streptomyces viridochromogenes. | Zea mays L. (maize) |
| A-181 | TC1507 | Mycogen (c/o Dow AgroSciences); Pioneer (c/o Dupont) | Insect-resistant and glufosinate ammonium herbicide tolerant maize produced by inserting the cry1F gene from Bacillus thuringiensis var. aizawai and the phosphinothricin N-acetyltransferase encoding gene from Streptomyces viridochromogenes. | Zea mays L. (maize) |
| A-182 | TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due to the presence of the cry1F gene from Bacillus thuringiensis var. aizawai. Corn rootworm-resistance is derived from DAS-59122-7 which contains the cry34Ab1 and cry35Ab1 genes from Bacillus thuringiensis strain PS149B1. Tolerance to glufosinate ammonium herbcicide is derived from TC1507 from the phosphinothricin N-acetyltransferase encoding gene from Streptomyces viridochromogenes. | Zea mays L. (maize) |
| A-183 | VIP1034 | | Insect resistance; WO 03/052073 | Zea mays L. (maize) |

In one embodiment of the invention, the plants A-1 to A-183 of Table A, in total, or parts thereof, or propagation material of said plants are treated or contacted with the active compound combinations of the invention.

TABLE B

Non-exhaustive list of transgenic plants to work the invention from the APHIS database
of the United States Department of Agriculture (USDA). The database can be found on:
http://www.aphis.usda.gov/animal_welfare/efoia/index.shtml.

| No. | Petition | Extension of Petition Number | Institution | Plant | Trans-formation Event or Line | EA find conclusion & determination |
|---|---|---|---|---|---|---|
| B-1 | 10-070-01p | | Virginia Tech | Peanut | Sclerotinia blight resistant | N70, P39, and W171 |
| B-2 | 09-349-01p | | Dow AgroSciences | Soya bean | 2,4-D and glufosinate tolerant | DAS-68416-4 |
| B-3 | 09-328-01p | | Bayer Crop Science | Soya bean | glyphosate and isoxaflutole tolerant | FG72 |
| B-4 | 09-233-01p | | Dow | Corn | 2,4-D and ACCase-inhibitor tolerant | DAS-40278-9 |
| B-5 | 09-201-01p | | Monsanto | Soya bean | improved fatty acid profile | MON-877Ø5-6 |
| B-6 | 09-183-01p | | Monsanto | Soya bean | stearidonic acid produced | MON-87769 |
| B-7 | 09-082-01p | | Monsanto | Soya bean | Lepidopteran resistant | MON 87701 |
| B-8 | 09-063-01p | | Stine Seed | Corn | Glyphosate tolerant | HCEM485 |
| B-9 | 09-055-01p | | Monsanto | Corn | Drought Tolerant | MON 87460 |
| B-10 | 09-015-01p | | BASF Plant Science, LLC | Soya bean | imidazolinone tolerant | BPS-CV127-9 Soya bean |
| B-11 | 08-366-01p | | ArborGen | Eucalyptus | Freeze Tolerant, Fertility Altered | ARB-FTE1-08 |

TABLE B-continued

Non-exhaustive list of transgenic plants to work the invention from the APHIS database of the United States Department of Agriculture (USDA). The database can be found on: http://www.aphis.usda.gov/animal_welfare/efoia/index.shtml.

| No. | Petition | Extension of Petition Number | Institution | Plant | Trans-formation Event or Line | EA find conclusion & determination |
|---|---|---|---|---|---|---|
| B-12 | 08-340-01p | | Bayer | Cotton | Glufosinate Tolerant, Insect Resistant | T304-40XGHB 119 |
| B-13 | 08-338-01p | | Pioneer | Corn | Male Sterile, Fertility Restored, Visual Marker | DP-32138-1 |
| B-14 | 08-315-01p | | Florigene | Rose | Altered Flower Color | IFD-524Ø1-4 and IFD-529Ø1-9 |
| B-15 | 07-108-01p | | Syngenta | Cotton | *Lepidopteran* Resistant | COT67B |
| B-16 B-17 | 06-354-01p | | Pioneer | Soya bean | High Oleic Acid | DP-3Ø5423-1 |
| B-18 B-19 | 05-280-01p | | Syngenta | Corn | Thermostable alpha-amylase | 3272 |
| B-20 B-21 B-22 B-23 | 04-110-01p | | Monsanto & Forage Genetics | Alfalfa | Glyphosate Tolerant | J101, J163 |
| B-24 B-25 B-26 B-27 B-28 B-29 | 03-104-01p | | Monsanto & Scotts | Creeping bentgrass | Glyphosate Tolerant | ASR368 |
| B-30 B-31 | 07-253-01p | | Syngenta | Corn | *Lepidopteran* resistant | MIR-162 Maize |
| B-32 B-33 | 07-152-01p | | Pioneer | Corn | glyphosate & Imidazolinone tolerant | DP-098140-6 |
| B-34 B-35 | 04-337-01p | | University of Florida | Papaya | Papaya Ringspot Virus Resistant | X17-2 |
| B-36 B-37 | 06-332-01p | | Bayer CropScience | Cotton | Glyphosate tolerant | GHB614 |
| B-38 B-39 | 06-298-01p | | Monsanto | Corn | European Corn Borer resistant | MON 89034 |
| B-40 B-41 | 06-271-01p | | Pioneer | Soya bean | Glyphosate & acetolactate synthase tolerant | 356043 (DP 356Ø43-5) |
| B-42 B-43 | 06-234-01p | 98-329-01p | Bayer CropScience | Rice | Phosphinothricin tolerant | LLRICE601 |
| B-44 B-45 | 06-178-01p | | Monsanto | Soya bean | Glyphosate tolerant | MON 89788 |
| B-46 B-47 B-48 | 04-362-01p | | Syngenta | Corn | Corn Rootworm Protected | MIR604 |
| B-49 B-50 | 04-264-01p | | ARS | Plum | Plum Pox Virus Resistant | C5 |
| B-51 B-52 | 04-229-01p | | Monsanto | Corn | High Lysine | LY038 |
| B-53 B-54 | 04-125-01p | | Monsanto | Corn | Corn Rootworm Resistant | 88017 |
| B-55 B-56 B-57 | 04-086-01p | | Monsanto | Cotton | Glyphosate Tolerant | MON 88913 |
| B-58 B-59 | 03-353-01p | | Dow | Corn | Corn Rootworm Resistant | 59122 |
| B-60 B-61 | 03-323-01p | | Monsanto | Sugar Beet | Glyphosate Tolerant | H7-1 TC-6275 |
| B-62 B-63 | 03-181-01p | 00-136-01p | Dow | Corn | *Lepidopteran* Resistant & Phosphinothricin tolerant | |
| B-64 B-65 | 03-155-01p | | Syngenta | Cotton | *Lepidopteran* Resistant | COT 102 |
| B-66 B-67 | 03-036-01p | | Mycogen/Dow | Cotton | *Lepidopteran* Resistant | 281-24-236 |
| B-68 B-69 | 03-036-02p | | Mycogen/Dow | Cotton | *Lepidopteran* Resistant | 3006-210-23 |
| B-70 | 02-042-01p | | Aventis | Cotton | Phosphinothricin tolerant | LLCotton25 |

TABLE B-continued

Non-exhaustive list of transgenic plants to work the invention from the APHIS database of the United States Department of Agriculture (USDA). The database can be found on: http://www.aphis.usda.gov/animal_welfare/efoia/index.shtml.

| No. | Petition | Extension of Petition Number | Institution | Plant | Trans-formation Event or Line | EA find conclusion & determination |
|---|---|---|---|---|---|---|
| B-71 | 01-324-01p | 98-216-01p | Monsanto | Rapeseed | Glyphosate tolerant | RT200 |
| B-72 | 01-206-01p | 98-278-01p | Aventis | Rapeseed | Phosphinothricin tolerant & pollination control | MS1 & RF1/RF2 |
| B-73 | 01-206-02p | 97-205-01p | Aventis | Rapeseed | Phosphinothricin tolerant | Topas19/2 |
| B-74 | 01-137-01p | | Monsanto | Corn | Corn Rootworm Resistant | MON 863 |
| B-75 | 01-121-01p | | Vector | Tobacco | Reduced nicotine | Vector 21-41 |
| B-76 | 00-342-01p | | Monsanto | Cotton | *Lepidopteran* resistant | Cotton Event 15985 |
| B-77 | 00-136-01p | | Mycogen c/o Dow & Pioneer | Corn | *Lepidopteran* resistant phosphinothricin tolerant | Line 1507 |
| B-78 | 00-011-01p | 97-099-01p | Monsanto | Corn | Glyphosate tolerant | NK603 |
| B-79 | 99-173-0 1p | 97-204-01p | Monsanto | Potato | PLRV & CPB resistant | RBMT22-82 |
| B-80 | 98-349-01p | 95-228-01p | AgrEvo | Corn | Phosphinothricin tolerant and Male sterile | MS6 |
| B-81 | 98-335-01p | | U. of Saskatchewan | Flax | Tolerant to soil residues of sulphonyl urea herbicide | CDC Triffid |
| B-82 | 98-329-01p | | AgrEvo | Rice | Phosphinothricin tolerant | LLRICE06, LLRICE62 |
| B-83 | 98-278-01p | | AgrEvo | Rapeseed | Phosphinothricin tolerant & Pollination control | MS8 & RF3 |
| B-84 | 98-238-01p | | AgrEvo | Soya bean | Phosphinothricin tolerant | GU262 |
| B-85 | 98-216-01p | | Monsanto | Rapeseed | Glyphosate tolerant | RT73 |
| B-86 | 98-173-01p | | Novartis Seeds & Monsanto | Beet | Glyphosate tolerant | GTSB77 |
| B-87 | 98-014-01p | 96-068-01p | AgrEvo | Soya bean | Phosphinothricin tolerant | A5547-127 |
| B-88 | 97-342-01p | | Pioneer | Corn | Male sterile & Phosphinothricin tolerant | 676, 678, 680 |
| B-89 | 97-339-01p | | Monsanto | Potato | CPB & PVY resistant | RBMT15-101, SEMT15-02, SEMT15-15 |
| B-90 | 97-336-01p | | AgrEvo | Beet | Phosphinothricin tolerant | T-120-7 |
| B-91 | 97-287-01p | | Monsanto | Tomato | *Lepidopteran* resistant | 5345 |
| B-92 | 97-265-01p | | AgrEvo | Corn | Phosphinothricin tolerant & *Lepidopteran* resistant | CBH-351 |
| B-93 | 97-205-01p | | AgrEvo | Rapeseed | Phosphinothricin tolerant | T45 |
| B-94 | 97-204-01p | | Monsanto | Potato | CPB & PLRV resistant | RBMT21-129 & RBMT21-350 |
| B-95 | 97-148-01p | | Bejo | *Cichorium intybus* | Male sterile | RM3-3, RM3-4, RM3-6 |
| B-96 | 97-099-01p | | Monsanto | Corn | Glyphosate tolerant | GA21 |
| B-97 | 97-013-01p | | Calgene | Cotton | Bromoxynil tolerant & *Lepidopteran* resistant | Events 31807 & 31808 |
| B-98 | 97-008-01p | | Du Pont | Soya bean | Oil profile altered | G94-1, G94-19, G-168 |

TABLE B-continued

Non-exhaustive list of transgenic plants to work the invention from the APHIS database of the United States Department of Agriculture (USDA). The database can be found on: http://www.aphis.usda.gov/animal_welfare/efoia/index.shtml.

| No. | Petition | Extension of Petition Number | Institution | Plant | Trans-formation Event or Line | EA find conclusion & determination |
|---|---|---|---|---|---|---|
| B-99 | 96-317-01p | | Monsanto | Corn | Glyphosate tolerant & ECB resistant | MON802 |
| B-100 | 96-291-01p | | DeKalb | Corn | European Corn Borer resistant | DBT418 |
| B-101 | 96-248-01p | 92-196-01p | Calgene | Tomato | Fruit ripening altered | 1 additional FLAVRSAVR line |
| B-102 | 96-068-01p | | AgrEvo | Soya bean | Phosphinothricin tolerant | W62, W98, A2704-12, A2704-21, A5547-35 |
| B-103 | 96-051-01p | | Cornell U | Papaya | PRSV resistant | 55-1, 63-1 |
| B-104 | 96-017-01p | 95-093-01p | Monsanto | Corn | European Corn Borer resistant | MON809 & MON810 |
| B-105 | 95-352-01p | | Asgrow | Squash | CMV, ZYMV, WMV2 resistant | CZW-3 |
| B-106 | 95-338-01p | | Monsanto | Potato | CPB resistant | SBT02-5 & -7, ATBT04-6 &-27, -30, -31, -36 |
| B-107 | 95-324-01p | | Agritope | Tomato | Fruit ripening altered | 35 1 N |
| B-108 | 95-256-01p | | Du Pont | Cotton | Sulfonylurea tolerant | 19-51a |
| B-109 | 95-228-01p | | Plant Genetic Systems | Corn | Male sterile | MS3 |
| B-110 | 95-195-01p | | Northrup King | Corn | European Corn Borer resistant | Bt11 |
| B-111 | 95-179-01p | 92-196-01p | Calgene | Tomato | Fruit ripening altered | 2 additional FLAVRSAVR lines |
| B-112 | 95-145-01p | | DeKalb | Corn | Phosphinothricin tolerant | B16 |
| B-113 | 95-093-01p | | Monsanto | Corn | *Lepidopteran* resistant | MON 80100 |
| B-114 | 95-053-01p | | Monsanto | Tomato | Fruit ripening altered | 8338 |
| B-115 | 95-045-01p | | Monsanto | Cotton | Glyphosate tolerant | 1445, 1698 |
| B-116 | 95-030-01p | 92-196-01p | Calgene | Tomato | Fruit ripening altered | 20 additional FLAVRSAVR lines |
| B-117 | 94-357-01p | | AgrEvo | Corn | Phosphinothricin tolerant | T14, T25 |
| B-118 | 94-319-01p | | Ciba Seeds | Corn | *Lepidopteran* resistant | Event 176 |
| B-119 | 94-308-01p | | Monsanto | Cotton | *Lepidopteran* resistant | 531, 757, 1076 |
| B-120 | 94-290-01p | | Zeneca & Petoseed | Tomato | Fruit polygalacturonase level decreased | B, Da, F |
| B-121 | 94-257-01p | | Monsanto | Potato | Coleopteran resistant | BT6, BT10, BT12, BT16, BT17, BT18, BT23 |
| B-122 | 94-230-01p | 92-196-01p | Calgene | Tomato | Fruit ripening altered | 9 additional FLAVRSAVR lines |
| B-123 | 94-228-01p | | DNA Plant Tech | Tomato | Fruit ripripening altered | 1345-4 |
| B-124 | 94-227-01p | 92-196-01p | Calgene | Tomato | Fruit ripening altered | Line N73 1436-111 |
| B-125 | 94-090-01p | | Calgene | Rapeseed | Oil profile altered | pCGN3828-212/86- 18 & 23 |
| B-126 | 93-258-01p | | Monsanto | Soya bean | Glyphosate tolerant | 40-3-2 |
| B-127 | 93-196-01p | | Calgene | Cotton | Bromoxynil tolerant | BXN |

TABLE B-continued

Non-exhaustive list of transgenic plants to work the invention from the APHIS database of the United States Department of Agriculture (USDA). The database can be found on: http://www.aphis.usda.gov/animal_welfare/efoia/index.shtml.

| No. | Petition | Extension of Petition Number | Institution | Plant | Trans-formation Event or Line | EA find conclusion & determination |
|---|---|---|---|---|---|---|
| B-128 | 92-204-01p | | Upjohn | Squash | WMV2 & ZYMV resistant | ZW-20 |
| B-129 | 92-196-01p | | Calgene | Tomato | Fruit ripening altered | FLAVR SAVR |

Abbreviations used in this table:
CMV-cucumber mosaic virus
CPB-colorado potato beetle
PLRV- potato leafroll virus
PRSV-papaya ringspot virus
PVY-potato virus Y
WMV2- watermelon mosaic virus 2
ZYMV-zucchini yellow mosaic virus In one embodiment of the invention, the plants B-1 to B-129 of Table B, in total, or parts thereof, or propagation material of said plants are treated or contacted with the active compound combinations of the invention.

TABLE C

Non-exhaustive list of traits to work the invention with reference to documents in which they are described.

| No. | Trait | Reference |
|---|---|---|
| C-1 | Water use efficiency | WO 2000/073475 |
| | | WO2009/150541 |
| C-2 | Nitrogen use efficiency | WO 1995/009911 |
| | | WO 1997/030163 |
| | | WO 2007/092704 |
| | | WO 2007/076115 |
| | | WO 2005/103270 |
| | | WO 2002/002776 |
| | | WO2008/051608 |
| | | WO2008/112613 |
| | | WO2009/015096 |
| | | WO2009/061776 |
| | | WO2009/105492 |
| | | WO2009/105612 |
| | | WO2009/117853 |
| | | WO2010/006010 |
| | | WO2009/117853 |
| | | WO2009/061776 |
| | | WO2009/015096 |
| | | WO2009/105492 |
| | | WO2009/105612 |
| | | WO2010/006010 |
| | | WO2010/007496 |
| C-3 | Improved photosynthesis | WO 2008/056915 |
| | | WO 2004/101751 |
| C-4 | Nematode resistance | WO 1995/020669 |
| | | WO 2001/051627 |
| | | WO 2008/139334 |
| | | WO 2008/095972 |
| | | WO 2006/085966 |
| | | WO 2003/033651 |
| | | WO 1999/060141 |
| | | WO 1998/012335 |
| | | WO 1996/030517 |
| | | WO 1993/018170 |
| | | WO2008/095886 |
| | | WO2008/095887 |
| | | WO2008/095888 |
| | | WO2008/095889 |
| | | WO2008/095910 |
| | | WO2008/095911 |
| | | WO2008/095916 |
| | | WO2008/095919 |
| | | WO2008/095969 |
| | | WO2008/095970 |
| | | WO2008/095972 |
| | | WO2008/110522 |
| | | WO2008/139334 |
| | | WO2008/152008 |
| | | WO2009/000736 |
| | | WO2009/065863 |
| | | WO2009/112505 |
| | | WO2009/132089 |
| | | WO2010/023186 |
| | | WO2010/025172 |
| | | WO2010/027793 |
| | | WO2010/027799 |
| | | WO2010/027804 |
| | | WO2010/027805 |
| | | WO2010/027808 |
| | | WO2010/027809 |
| C-5 | Reduced pod dehiscence | WO 2006/009649 |
| | | WO 2004/113542 |
| | | WO 1999/015680 |
| | | WO 1999/000502 |
| | | WO 1997/013865 |
| | | WO 1996/030529 |
| | | WO 1994/023043 |
| C-6 | *Aphid* resistance | WO 2006/125065 |
| | | WO 1997/046080 |
| | | WO 2008/067043 |
| | | WO 2004/072109 |
| | | WO2009/091860 |
| | | WO 2009021153 |
| | | WO2010036764 |
| C-7 | *Sclerotinia* resistance | WO 2006/135717 |
| | | WO 2006/055851 |
| | | WO 2005/090578 |
| | | WO 2005/000007 |
| | | WO 2002/099385 |
| | | WO 2002/061043 |
| C-8 | *Botrytis* resistance | WO 2006/046861 |
| | | WO 2002/085105 |
| C-9 | *Bremia* resistance | US 20070022496 |
| | | WO 2000/063432 |
| | | WO 2004/049786 |
| | | WO2009/111627 |
| C10 | *Erwinia* resistance | WO 2004/049786 |
| C-11 | Closterovirus resistance | WO 2007/073167 |
| | | WO 2007/053015 |
| | | WO 2002/022836 |

TABLE C-continued

Non-exhaustive list of traits to work the invention with reference to documents in which they are described.

| No. | Trait | Reference |
|---|---|---|
| C-12 | Stress tolerance (including drought tolerance) | WO 2010/019838 |
| | | WO 2009/049110 |
| | | WO2008/002480 |
| | | WO2005/033318 |
| | | WO2008/002480 |
| | | WO2008/005210 |
| | | WO2008/006033 |
| | | WO2008/008779 |
| | | WO2008/022486 |
| | | WO2008/025097 |
| | | WO2008/027534 |
| | | WO2008/027540 |
| | | WO2008/037902 |
| | | WO2008/046069 |
| | | WO2008/053487 |
| | | WO2008/057642 |
| | | WO2008/061240 |
| | | WO2008/064222 |
| | | WO2008/064341 |
| | | WO2008/073617 |
| | | WO2008/074025 |
| | | WO2008/076844 |
| | | WO2008/096138 |
| | | WO2008/110848 |
| | | WO2008/116829 |
| | | WO2008/117537 |
| | | WO2008/121320 |
| | | WO2008/125245 |
| | | WO2008/142034 |
| | | WO2008/142036 |
| | | WO2008/150165 |
| | | WO2008/092935 |
| | | WO2008/145675 |
| | | WO2009/010460 |
| | | WO2009/016240 |
| | | WO2009/031664 |
| | | WO2009/038581 |
| | | WO2009/049110 |
| | | WO2009/053511 |
| | | WO2009/054735 |
| | | WO2009/067580 |
| | | WO2009/073605 |
| | | WO2009/077611 |
| | | WO2009/079508 |
| | | WO2009/079529 |
| | | WO2009/083958 |
| | | WO2009/086229 |
| | | WO2009/092009 |
| | | WO2009/094401 |
| | | WO2009/094527 |
| | | WO2009/102965 |
| | | WO2009/114733 |
| | | WO2009/117448 |
| | | WO2009/126359 |
| | | WO2009/126462 |
| | | WO2009/129162 |
| | | WO2009/132057 |
| | | WO2009/141824 |
| | | WO2009/148330 |
| | | WO2010/037714 |
| | | WO2010/031312 |
| | | WO2010/006010 |
| | | WO2010/007495 |
| | | WO2010/019838 |
| | | WO2010/025513 |
| C-13 | Tobamovirus resistance | WO 2006/038794 |
| | | WO2002081713 |
| | | WO2009086850 |
| C-14 | Harvest yield | WO2008/125983A2 |
| | | WO2008/112613A1 |
| | | WO2008/118394A1 |
| | | WO2008/015263A2 |
| | | WO2008/021021A2 |
| | | WO2008/043849A2 |
| | | WO2008/044150A2 |
| | | WO2008/049183A1 |
| | | WO2008/056915A1 |
| | | WO2008/059048A1 |
| | | WO2008/062049A1 |
| | | WO2008/071767A1 |
| | | WO2008/074891A2 |
| | | WO2008/087932A1 |
| | | WO2008/092910A1 |
| | | WO2008/092935A2 |
| | | WO2008/104598A2 |
| | | WO2008/111779A1 |
| | | WO2008/122980A2 |
| | | WO2008/135206A2 |
| | | WO2008/135467A2 |
| | | WO2008/135603A2 |
| | | WO2008/137108A2 |
| | | WO2008/138975A1 |
| | | WO2008/142146A1 |
| | | WO2008/142163A2 |
| | | WO2008/145629A2 |
| | | WO2008/145675A2 |
| | | WO2008/145761A1 |
| | | WO2008/148872A1 |
| | | WO2008/073617A2 |
| | | WO2009//127671A1 |
| | | WO2009/0 65912A2 |
| | | WO2009/000789A1 |
| | | WO2009/000848A1 |
| | | WO2009/000876A1 |
| | | WO2009/003977A2 |
| | | WO2009/009142A2 |
| | | WO2009/012467A2 |
| | | WO2009/013225A2 |
| | | WO2009/013263A2 |
| | | WO2009/014665A2 |
| | | WO2009/016104A1 |
| | | WO2009/016212A2 |
| | | WO2009/016232A2 |
| | | WO2009/021548A1 |
| | | WO2009/034188A1 |
| | | WO2009/037279A1 |
| | | WO2009/037329A2 |
| | | WO2009/037338A1 |
| | | WO2009/040665A2 |
| | | WO2009/056566A2 |
| | | WO2009/060040A1 |
| | | WO2009/068564A1 |
| | | WO2009/068588A2 |
| | | WO2009/072676A1 |
| | | WO2009/073069A2 |
| | | WO2009/075860A2 |
| | | WO2009/077973A1 |
| | | WO2009/080743A2 |
| | | WO2009/080802A2 |
| | | WO2009/091518A2 |
| | | WO2009/092772A2 |
| | | WO2009/095455A1 |
| | | WO2009/095641A2 |
| | | WO2009/095881A2 |
| | | WO2009/097133A2 |
| | | WO2009/102978A2 |
| | | WO2009/106596A2 |
| | | WO2009/108513A2 |
| | | WO2009/113684A1 |
| | | WO2009/134339A2 |
| | | WO2009/135130A2 |
| | | WO2009/135810A1 |
| | | WO2009/145290A1 |
| | | WO2009/150170A1 |
| | | WO2009/153208A1 |
| | | WO2009/156360A1 |
| | | WO2010/012796A1 |
| | | WO2010/003917A1 |
| | | WO2010/037228A1 |
| | | WO2010/000794A1 |

TABLE C-continued

Non-exhaustive list of traits to work the invention with reference to documents in which they are described.

| No. | Trait | Reference |
|---|---|---|
| | | WO2010/005298A2 |
| | | WO2010/006732A2 |
| | | WO2010/007035A1 |
| | | WO2010/007496A2 |
| | | WO2010/012760A2 |
| | | WO2010/019872A1 |
| | | WO2010/023310A2 |
| | | WO2010/023320A2 |
| | | WO2010/025465A1 |
| | | WO2010/025466A2 |
| | | WO2010/028205A1 |
| | | WO2010/028456A1 |
| | | WO2010/033564A1 |
| | | WO2010/034652A1 |
| | | WO2010/034672A1 |
| | | WO2010/034681A1 |
| | | WO2010/035784A1 |
| | | WO2010/036866A1 |
| | | WO2010/039750A2 |

In one embodiment of the invention, the plants comprising or expressing traits of C-1 to C-14 of Table C, in total, or parts thereof, or propagation material of said plants are treated or contacted with the active compound combinations of the invention.

TABLE D

Non-exhaustive list of transgenic events and traits the invention can be worked on with reference to patent applications.

| No. | Plant species | Transgenic event | Trait | Patent reference |
|---|---|---|---|---|
| D-1 | Maize | PV-ZMGT32 (NK603) | Glyphosate tolerance | US 2007-056056 |
| D-2 | Maize | MIR604 | Insect resistance (Cry3a055) | EP-A 1 737 290 |
| D-3 | Maize | LY038 | High lysine content | U.S. Pat. No. 7,157,281 |
| D-4 | Maize | 3272 | Self processing corn (alpha-amylase) | US 2006-230473 |
| D-5 | Maize | PV-ZMIR13 (MON863) | Insect resistance (Cry3Bb) | US 2006-095986 |
| D-6 | Maize | DAS-59122-7 | Insect resistance (Cry34Ab1/Cry35Ab1) | US 2006-070139 |
| D-7 | Maize | TC1507 | Insect resistance (Cry1F) | U.S. Pat. No. 7,435,807 |
| D-8 | Maize | MON810 | Insect resistance (Cry1Ab) | US 2004-180373 |
| D-9 | Maize | VIP1034 | Insect resistance | WO 03/052073 |
| D-10 | Maize | B16 | Glufosinate resistance | US 2003-126634 |
| D-11 | Maize | GA21 | Glyphosate resistance | U.S. Pat. No. 6,040,497 |
| D-12 | Maize | GG25 | Glyphosate resistance | U.S. Pat. No. 6,040,497 |
| D-13 | Maize | GJ11 | Glyphosate resistance | U.S. Pat. No. 6,040,497 |
| D-14 | Maize | FI117 | Glyphosate resistance | U.S. Pat. No. 6,040,497 |
| D-15 | Maize | GAT-ZM1 | Glufosinate tolerance | WO 01/51654 |
| D-16 | Maize | DP-098140-6 | Glyphosate tolerance/ ALS inhibitor tolerance | WO 2008/112019 |
| D-17 | Wheat | Event 1 | Fusarium resistance (trichothecene 3-O-acetyltransferase) | CA 2561992 |
| D-18 | Sugar beet | T227-1 | Glyphosate tolerance | US 2004-117870 |
| D-19 | Sugar beet | H7-1 | Glyphosate tolerance | WO 2004-074492 |
| D-20 | Soybean | MON89788 | Glyphosate tolerance | US 2006-282915 |
| D-21 | Soybean | A2704-12 | Glufosinate tolerance | WO 2006/108674 |
| D-22 | Soybean | A5547-35 | Glufosinate tolerance | WO 2006/108675 |
| D-23 | Soybean | DP-305423-1 | High oleic acid/ALS inhibitor tolerance | WO 2008/054747 |
| D-24 | Rice | GAT-OS2 | Glufosinate tolerance | WO 01/83818 |
| D-25 | Rice | GAT-OS3 | Glufosinate tolerance | US 2008-289060 |
| D-26 | Rice | PE-7 | Insect resistance (Cry1Ac) | WO 2008/114282 |
| D-27 | Oilseed rape | MS-B2 | Male sterility | WO 01/31042 |
| D-28 | Oilseed rape | MS-BN1/RF-BN1 | Male sterility/restoration | WO 01/41558 |
| D-29 | Oilseed rape | RT73 | Glyphosate resistance | WO 02/36831 |
| D-30 | Cotton | CE43-67B | Insect resistance (Cry1Ab) | WO 2006/128573 |
| D-31 | Cotton | CE46-02A | Insect resistance (Cry1Ab) | WO 2006/128572 |
| D-32 | Cotton | CE44-69D | Insect resistance (Cry1Ab) | WO 2006/128571 |
| D-33 | Cotton | 1143-14A | Insect resistance (Cry1Ab) | WO 2006/128569 |
| D-34 | Cotton | 1143-51B | Insect resistance (Cry1Ab) | WO 2006/128570 |
| D-35 | Cotton | T342-142 | Insect resistance (Cry1Ab) | WO 2006/128568 |
| D-36 | Cotton | event3006-210-23 | Insect resistance (Cry1Ac) | WO 2005/103266 |
| D-37 | Cotton | PV-GHGT07 (1445) | Glyphosate tolerance | US 2004-148666 |
| D-38 | Cotton | MON88913 | Glyphosate tolerance | WO 2004/072235 |
| D-39 | Cotton | EE-GH3 | Glyphosate tolerance | WO 2007/017186 |
| D-40 | Cotton | T304-40 | Insect-resistance (Cry1Ab) | WO2008/122406 |
| D-41 | Cotton | Cot202 | Insect resistance (VIP3) | US 2007-067868 |
| D-42 | Cotton | LLcotton25 | Glufosinate resistance | WO 2007/017186 |

TABLE D-continued

Non-exhaustive list of transgenic events and traits the invention can be worked on with reference to patent applications.

| No. | Plant species | Transgenic event | Trait | Patent reference |
|---|---|---|---|---|
| D-43 | Cotton | EE-GH5 | Insect resistance (Cry1Ab) | WO 2008/122406 |
| D-44 | Cotton | event 281-24-236 | Insect resistance (Cry1F) | WO 2005/103266 |
| D-45 | Cotton | Cot102 | Insect resistance (Vip3A) | US 2006-130175 |
| D-46 | Cotton | MON 15985 | Insect resistance (Cry1A/Cry2Ab) | US 2004-250317 |
| D-47 | Bentgrass | Asr-368 | Glyphosate tolerance | US 2006-162007 |
| D-48 | Aubergine | EE-1 | Insect resistance (Cry1Ac) | WO 2007/091277 |

In one embodiment, the plants comprising a transgenic event or expressing a trait of D-1 to D-48 of Table D, in total, or parts thereof, or propagation material of said plants are treated or contacted with the active compound combinations of the invention.

TABLE E

Non-exhaustive list of transgenic events and traits and their trade names.

| No. | Trade name | Plant | Company | Genetically modified properties | Additional information |
|---|---|---|---|---|---|
| E-1 | Roundup Ready ® | *Beta vulgaris* (sugar beet) | Monsanto Company | Glyphosate tolerance | |
| E-2 | InVigor ® | *Brassica napus* (Argentine canola) | Bayer CropScience | Canola rape was genetically modified with the following result: Ø expression of a gene which confers tolerance to the herbicide glyfosinate-ammonium; Ø introduction of a novel hybrid breeding system for canola rape which is based on genetically modified male-sterility (MS) and fertility-restorer (RF) lines; Ø expression of a gene for resistance to antibiotics | |
| E-3 | Liberty Link ® | *Brassica napus* (Argentine canola) | BayerCropScience | Phosphinothricin tolerance | |
| E-4 | Roundup Ready ® | *Brassica napus* (Canola rape) | Monsanto Company | Glyphosate tolerance | |
| E-5 | Clearfield ® | (Canola rape) | BASF Corporation | Non-GMO, imazamox tolerance | |
| E-6 | Optimum ™ GAT ™ | *Glycine max* L. (soybean) | Pioneer Hi-Bred International, Inc | Glyphosate and ALS herbicide tolerance | |
| E-7 | Roundup Ready ™ | *Glycine max* L. (soybean) | Monsanto Company | Glyphosate tolerance | |
| E-8 | Roundup RReady2Yiel ™ | *Glycine max* L. (soybean) | Monsanto Company | Glyphosate tolerance | |
| E-9 | STS ® | *Glycine max* L. (soybean) | DuPont | Sulfonylurea tolerance | |
| E-10 | YIELD GARD ® | *Glycine max* L. (soybean) | Monsanto Company | | |
| E-11 | AFD ® | *Gossypium hirsutum* L. (cotton) | Bayer CropScience | The lines include, for example, AFD5062LL, AFD5064F, AFD5065B2F; AFD seed is available in a wide range of varieties with integrated technology such as, for example, the Bollgard ®, Bollgard II, Roundup Ready, Roundup Ready Flex and LibertyLink ® technologies | |
| E-12 | Bollgard II ® | *Gossypium hirsutum* L. (cotton) | Monsanto Company | MON 15985 event: Cry2(A)b1; Cry1A(c) | |

TABLE E-continued

Non-exhaustive list of transgenic events and traits and their trade names.

| No. | Trade name | Plant | Company | Genetically modified properties | Additional information |
|---|---|---|---|---|---|
| E-13 | Bollgard ® | *Gossypium hirsutum* L. (cotton) | Monsanto Company | Cry 1Ac | |
| E-14 | FiberMax ® | *Gossypium hirsutum* L. (cotton) | Bayer CropScience | | |
| E-15 | Liberty Link ® | *Gossypium hirsutum* L. (cotton) | Bayer CropScience | Phosphinothricin tolerance | |
| E-16 | Nucotn 33B | *Gossypium hirsutum* L. (cotton) | Delta Pine and Land | Bt toxin in the lines from Delta Pine: Cry1Ac | |
| E-17 | Nucotn 35B | *Gossypium hirsutum* L. (cotton) | Delta Pine and Land | Bt toxin in the lines from Delta Pine: Cry1Ac | |
| E-18 | Nucotn ® | *Gossypium hirsutum* L. (cotton) | Delta Pine and Land | Bt toxin in the lines from Delta Pine | |
| E-19 | PhytoGeu ™ | *Gossypium hirsutum* L. (cotton) | PhytoGen Seed Company, Dow AgroSciences LLC | Comprises varieties which contain, for example, Roundup Ready flex, Widestrike | |
| E-20 | Roundup Ready Flex ® | *Gossypium hirsutum* L. (cotton) | Monsanto Company | Glyphosate tolerance | |
| E-21 | Roundup Ready ® | *Gossypium hirsutum* L. (cotton) | Monsanto Company | Glyphosate tolerance | |
| E-22 | Widesirike ™ | *Gossypium hirsutum* L. (cotton) | Dow AgroSciences LLC | Cry1F and Cry1Ac | Monsanto/Dow |
| E-23 | YIELD GARD ® | *Gossypium hirsutum* L. (cotton) | Monsanto Company | | http://www.garstseed.com/ GarstClient/Technology/agrisure.aspx |
| E-24 | Roundup Ready ® | *Medicago sativa* (alfalfa) | Monsanto Company | Glyphosate tolerance | |
| E-25 | Clearfield ® | *Oryza sativa* (rice) | BASF Corporation | Non-GMO, imazamox tolerance | |
| E-26 | NewLeaf ® | *Solanum tuberosum* L. (potato) | Monsanto Company | Resistance to infection by potato leafroll virus (PLRV) and feeding damage by the Colorado beetle *Leptinotarsa decemlineata* | |
| E-27 | NewLeaf ® plus | *Solanum tuberosum* L. (potato) | Monsanto Company | Resistance to infection by potato leafroll virus (PLRV) and feeding damage by the Colorado beetle *Leptinotarsa decemlineata* | http://www.dowagro.com/ phytogen/index.htm |
| E-28 | Protecta ® | *Solanum tuberosum* L. (potato) | | | |
| E-29 | Clearfield ® | Sunflower | BASF Corporation | Non-GMO, imazamox tolerance | |
| E-30 | Roundup Ready ® | *Triticum aestivum* (wheat) | Monsanto Company | Glyphosate tolerance, NK603 | |
| E-31 | Clearfield ® | Wheat | BASF Corporation | Non-GMO, imazamox tolerance | |
| E-32 | Agrisure ® (family) | *Zea mays* L. (maize) | Syngenta Seeds, Inc. | These include Agrisure CB/LL (BT 11 event plus phosphinothricin tolerance as the result of GA21 event); Agrisure CB/LL/RW (Bt 11 event, modified synthetic Cry3A gene, phosphinothricin tolerance as the result of GA21 event); Agrisure GT (glyphosate tolerance); Agrisure GT/CB/LL (glyphosate and phosphinothricin tolerance as the result of GA21 event, Bt 11 event); | |

TABLE E-continued

Non-exhaustive list of transgenic events and traits and their trade names.

| No. | Trade name | Plant | Company | Genetically modified properties | Additional information |
|---|---|---|---|---|---|
| | | | | Agrisure 3000GT (CB/LL/RW/GT: glyphosate and phosphinothricin tolerance as the result of GA21 event, Bt 11 event, modified synthetic Cry3A gene); Agrisure GT/RW (glyphosate tolerance, modified synthetic Cry3A gene); Agrisure RW (modified synthetic Cry3A gene); future traits | |
| E-33 | BiteGard ® | *Zea mays* L. (maize) | Novartis Seeds | cry1A(b) gene | |
| E-34 | Bt-Xtra ® | *Zea mays* L. (maize) | DEKALB Genetics Corporation | cry1Ac gene | |
| E-35 | Clearfield ® | *Zea mays* L. (maize) | BASF Corporation | Non-GMO, imazamox tolerance | |
| E-36 | Herculex ® (family) | *Zea mays* L. (maize) | Dow AgroSciences LLC | | |
| E-37 | IMI ® | *Zea mays* L. (maize) | DuPont | Imidazolinone tolerance | |
| E-38 | KnockOut ® | *Zea mays* L. (maize) | Syngenta Seeds, Inc. | SYN-EV176-9: cry1A(b) gene | |
| E-39 | Mavera ® | *Zea mays* L. (maize) | Renessen LLC | High-lysine | http://www.dowagro.com/widestrike/ |
| E-40 | NatureGard ® | *Zea mays* L. (maize) | Mycogen | cry1A(b) gene | |
| E-41 | Roundup Ready ® | *Zea mays* L. (maize) | Monsanto Company | Glyphosate tolerance | http://www.starlinkcorn.com/ starlinkcorn.htm |
| E-42 | Roundup Ready ® 2 | *Zea mays* L. (maize) | Monsanto Company | Glyphosate tolerance | |
| E-43 | SmartStax | *Zea mays* L. (maize) | Monsanto Company | Combination of eight genes | |
| E-44 | StarLink ® | *Zea mays* L. (maize) | Aventis CropScience -> Bayer CropScience | Cry9c gene | |
| E-45 | STS ® | *Zea mays* L. (maize) | DuPont | Sulfonylurea tolerance | |
| E-46 | YIELD GARD ® | *Zea mays* L. (maize) | Monsanto Company | Mon810, Cry1Ab1, resistance to the European corn borer | http://www.dowagro.com/herculex/ about/herculexfamily/ |
| E-47 | YieldGard ® Plus | *Zea mays* L. (maize) | Monsanto Company | Mon810xMon863, dual resistance to European corn borer and corn rootworm | |
| E-48 | YieldGard ® Rootworm | *Zea mays* L. (maize) | Monsanto Company | Mon863, Cry3Bb1, resistance to corn rootworm | |
| E-49 | YieldGard ® VT | *Zea mays* L. (maize) | Monsanto Company | Stacked traits | |
| E-50 | YieldMaker ™ | *Zea mays* L. (maize) | DEKALB Genetics Corporation | Contains Roundup Ready 2 technology, YieldGard VT, YieldGard Corn Borer, YieldGard Rootworm and YieldGard Plus | |

In one embodiment, the plants comprising a transgenic event or expressing a trait of E-1 to E-50 of Table E, in total, or parts thereof, or propagation material of said plants are treated or contacted with the active compound combinations of the invention.

The plants listed can be treated in a particularly advantageous manner in accordance with the invention with the active compound combinations of the invention. The preferred ranges stated above for the active compound combinations also apply to the treatment of these plants. Particular emphasis is given to the treatment of plants with the active compound combinations specifically mentioned in the present text.

The active compound combinations can be converted to the customary formulations, such as solutions, emulsions, wettable powders, suspensions, powders, dusts, pastes, soluble powders, granules, suspension-emulsion concentrates, natural materials impregnated with active compound, synthetic materials impregnated with active compound and microencapsulations in polymeric substances.

These formulations are produced in a known manner, for example by mixing the active compound with extenders, that is liquid solvents and/or solid carriers, optionally with the use of surfactants, that is emulsifiers and/or dispersants and/or foam-formers.

Suitable for use as auxiliaries are substances which are suitable for imparting to the active compound combination itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolyzates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%, and in addition preferably extenders and/or surfactants.

The active compound content of the use forms prepared from the commercially available formulations can vary within wide limits. The active compound concentration of the use forms can be from 0.0000001 to 95% by weight of active compound, preferably between 0.0001 and 1% by weight.

Application is in a manner appropriate for the use forms.

The good insecticidal and/or acaricidal activity of the active compound combinations is illustrated by the examples below. Whereas the individual active compounds show weaknesses in their activity, the combinations show an activity which exceeds a simple addition of activities.

A synergistic effect in insecticides/acaricides is always present when the activity of the active compound combinations exceeds the total of the activities of the active compounds when applied individually. The expected activity for a given combination of two active compounds can be calculated according to S. R. Colby, Weeds 15 (1967), 20-22 as follows:

If
X is the kill rate, expressed in % of the untreated control, when active compound A is applied at an application rate of m g/ha or at a concentration of m ppm,
Y is the kill rate, expressed in % of the untreated control, when active compound B is applied at an application rate of n g/ha or at a concentration of n ppm and
E is the kill rate, expressed in % of the untreated control, when active compounds A and B are applied at application rates of m and n g/ha or at a concentration of m and n ppm, then $$E = X + Y - \frac{X \cdot Y}{100}$$

If the actual insecticidal kill rate is greater than calculated, the kill of the combination is superadditive, i.e. there is a synergistic effect. In this case, the actual observed kill rate has to be greater than the value for the expected kill rate (E) calculated from the formula given above.

USE EXAMPLES

Example A

*Aphis gossypii* Test

To produce a suitable preparation of active compound, the desired formulation is mixed with water and the concentrate is diluted with water to the desired concentration.

Individually potted conventional or transgenic—comprising a gene coding for herbicide resistance—cotton plants heavily infested by the cotton aphid (*Aphis gossypii*) are treated by spraying with the active compound preparation of the desired concentration.

After the desired period of time, the kill in % is determined. 100% means that all aphids have been killed; 0% means that no aphids have been killed. The kill rates determined are entered into Colby's formula (see Sheet 1).

In this test, for example, the following active compound combination in accordance with the present application shows a synergistically enhanced activity compared to the active compounds applied individually:

TABLE A1

*Aphis gossypii* test

| Active compound/event | Concentration in g of ai/ha | Activity in % after $3^d$ |
|---|---|---|
| cotton comprising GHB614 | | 0 |
| Dyne-Amic | 0.1% | 0 |
| spirotetramat SC 240 on conventional cotton | 75 | 0 |
| spirotetramat SC 240 + 0.1% Dyne-Amic on conventional cotton | 75 + 0.1% | 40 |
| Roundup Ultramax SL 450 (Glyphosate) on conventional cotton | 1541 | 35 (PTX 45%) |

| | found* | calc.** |
|---|---|---|
| spirotetramat + glyphosate on conventional cotton | 75 + 1541 | PTX |
| spirotetramat SC 240 on cotton comprising GHB614 | 75 | 5 |
| spirotetramat SC 240 + 0.1% Dyne-Amic on cotton comprising GHB614 | 75 + 0.1% | 20 |
| Roundup Ultramax SL 450 (glyphosate) on cotton comprising GHB614 | 1541 | 0 |

| | found* | calc.** |
|---|---|---|
| spirotetramat + glyphosate on cotton comprising GHB614 according to the invention | 75 + 1541 | 50 | 5 |

*found = activity found
**calc. = activity calculated using Colby's formula
PTX = plant damage
Spirotetramat = A.2

TABLE A2

*Aphis gossypii* test

| Active compound/event | Concentration in g of ai/ha | Activity in % after $4^d$ |
|---|---|---|
| cotton comprising GHB614 | | 0 |
| spirotetramat SC 240 on conventional cotton | 100 | 15 |
| spirotetramat SC 240 on cotton comprising GHB614 | 100 | 0 |
| Roundup Ultramax SL 450 (glyphosate) on conventional cotton | 1541 | PTX |
| Roundup Ultramax SL 450 (glyphosate) on cotton comprising GHB614 | 1541 | 25 |

| | found* | calc.** |
|---|---|---|
| spirotetramat + glyphosate on conventional cotton | 100 + 1541 | PTX |
| spirotetramat + glyphosate on cotton comprising GHB614 according to the invention | 100 + 1541 | 65 | 25 |

*found = activity found
**calc. = activity calculated using Colby's formula

TABLE A3

*Aphis gossypii* test

| Active compound/event | Concentration in g of ai/ha | Activity in % after $4^d$ |
|---|---|---|
| cotton comprising T304-40 X GHB119 | | 0 |
| spirotetramat SC 240 on conventional cotton | 100 | 15 |
| spirotetramat SC 240 on cotton comprising T304-40 X GHB119 | 100 | 0 |
| Ignite 280 SL (glufosinate-ammonium) on conventional cotton | 125 | PTX |
| Ignite 280 SL (glufosinate-ammonium) on cotton comprising T304-40 X GHB119 | 125 | 25 |

| | found* | calc.** |
|---|---|---|
| spirotetramat + glufosinate-ammonium on conventional cotton | 100 + 125 | PTX |
| spirotetramat + glufosinate-ammonium on cotton comprising T304-40 X GHB119 according to the invention | 100 + 125 | 60 | 25 |

*found = activity found
**calc. = activity calculated using Colby's formula

The invention claimed is:

1. An active compound composition comprising compound (A) and one or more compounds of group (B)

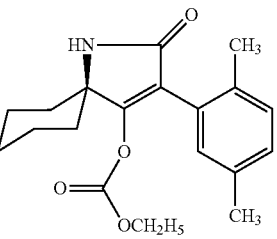

(A)

and
(B),
glufosinate, glufosinate-ammonium, glufosinate-P, glufosinate-P-ammonium, glufosinate-P-sodium, glyphosate, and glyphosate-isopropylammonium,
wherein the active components consists of (A) and (B) and wherein the weight ratio of (A) to (B) is 1:100 to 100:1.

2. An active compound composition according to claim 1, further comprising at least one of the safeners: benoxacor, cloquintocet, cyprosulfamide, dichlormid, fenclorim, fenchlorazole furilazole, isoxadifen, mefenpyr, 4-(dichloroacetyl)-1-oxa-4-azaspiro[4.5]decane, and 2,2,5-trimethyl-3-(dichloroacetyl)-1,3-oxazolidine.

3. A method for controlling an agricultural pest comprising applying a composition as defined in claim 2 to a plant and/or to an above-ground part of a plant.

4. An agrochemical composition comprising an active compound composition according to claim 1, and one or more extenders and/or surfactants.

5. A method for controlling an agricultural pest, comprising allowing an active compound composition according to claim 1 to act on an agricultural pest, and/or a habitat thereof.

6. A process for preparing an agrochemical composition, comprising mixing an active compound composition according to claim 1 with one or more extenders and/or surfactants.

7. A method for controlling an agriculture pest comprising applying a composition as defined in claim 1, to a plant and/or to an above-ground part of a plant.

8. A method for improving production potential of a transgenic plant by controlling an agricultural pest comprising treating the transgenic plant with an effective amount of an active compound composition according to claim 1.

9. A method according to claim 8, wherein the transgenic plant is a soya bean plant and/or a cotton plant.

10. An article comprising an active compound composition according to claim 1 and at least one transgenic plant.

11. The active compound composition according to claim 1 wherein component (B) comprises glyphosate.

12. The active compound composition according to claim 1, comprising a synergistically effective amount of components (A) and (B).

13. The active compound composition according to claim 1, wherein (B) comprises glufosinate.

14. The active compound composition according to claim 1, wherein the active components consists of spirotetramat and one or more of glufosinate and glyphosate, and which comprises a synergistically effective amount of components (A) and (B), and wherein the weight ratio of (A) to (B) is 1:100 to 100:1.

15. A method for controlling an agricultural pest, comprising allowing (A) spirotetramat and (B) one or more compounds of glufosinate, glufosinate-ammonium, glufosinate-P, glufosinate-P-ammonium, glufosinate-P-sodium, glyphosate, and glyphosate-isopropylammonium to act on an agricultural pest, and/or a habitat thereo, wherein the active components consists of (A) and (B) and wherein the weight ratio of (A) to (B) is 1:100 to 100:1.

16. A method according to claim 15, wherein the compounds act on a transgenic, glyphosate- or glufosinate-herbicide-resistant cotton plant.

17. A method according to claim 15, wherein insects are controlled.

* * * * *